United States Patent
Jiang et al.

(10) Patent No.: US 11,191,509 B2
(45) Date of Patent: Dec. 7, 2021

(54) SYSTEM AND METHOD FOR COMPUTED TOMOGRAPHY

(71) Applicant: SHANGHAI UNITED IMAGING HEALTHCARE CO., LTD., Shanghai (CN)

(72) Inventors: Yifeng Jiang, Shanghai (CN); Yingbiao Liu, Shanghai (CN); Yanfeng Du, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 16/939,161

(22) Filed: Jul. 27, 2020

(65) Prior Publication Data
US 2020/0352538 A1    Nov. 12, 2020

Related U.S. Application Data

(63) Continuation of application No. 15/638,610, filed on Jun. 30, 2017, now Pat. No. 10,722,204, which is a (Continued)

(30) Foreign Application Priority Data

Sep. 18, 2015  (CN) .......................... 201510598603.0
Sep. 30, 2015  (CN) .......................... 201510639797.4

(51) Int. Cl.
*A61B 6/00* (2006.01)
*A61B 6/03* (2006.01)
(Continued)

(52) U.S. Cl.
CPC .............. *A61B 6/5258* (2013.01); *A61B 6/03* (2013.01); *A61B 6/032* (2013.01); *A61B 6/0407* (2013.01);
(Continued)

(58) Field of Classification Search
CPC ................... A61B 6/032; A61B 6/582; G06T 2207/10081
See application file for complete search history.

(56) References Cited

U.S. PATENT DOCUMENTS

2003/0183771 A1  10/2003  Hirai
2007/0116183 A1  5/2007  Ueki et al.
(Continued)

FOREIGN PATENT DOCUMENTS

CN   1552288 A    12/2004
CN   102768759 A  11/2012
(Continued)

OTHER PUBLICATIONS

International Search Report in PCT/CN2016/099069 dated Nov. 29, 2016, 8 pages.
(Continued)

*Primary Examiner* — Dani Fox
(74) *Attorney, Agent, or Firm* — Metis IP LLC

(57) ABSTRACT

The present disclosure relates to a method and a system for computed tomography imaging. The method may comprise obtaining original data; obtaining a preprocessing result by preprocessing the original data; obtaining intensity of the artifact based on the preprocessing result; and updating a damaged channel or the air correction table based on the intensity of the artifact. Updating the air correction table may comprise: obtaining a first air correction table corresponding to a first temperature of detector; obtaining real-time temperature of detector; and obtaining a second air correction table corresponding to the real-time temperature based on the real-time temperature and the first air correction table.

20 Claims, 9 Drawing Sheets

Related U.S. Application Data continuation of application No. PCT/CN2016/099069, filed on Sep. 14, 2016.

(51) Int. Cl.
  *G06T 5/00* (2006.01)
  *A61B 6/04* (2006.01)

(52) U.S. Cl.
  CPC ............ *A61B 6/461* (2013.01); *A61B 6/5205* (2013.01); *A61B 6/54* (2013.01); *A61B 6/582* (2013.01); *G06T 5/00* (2013.01); *G06T 5/001* (2013.01); *A61B 6/037* (2013.01); *A61B 6/5264* (2013.01); *A61B 6/5282* (2013.01); *G06T 2207/10081* (2013.01)

(56) References Cited

U.S. PATENT DOCUMENTS

| | | |
|---|---|---|
| 2012/0002858 A1 | 1/2012 | Huang et al. |
| 2012/0250819 A1 | 10/2012 | Yoshida et al. |
| 2014/0014828 A1 | 1/2014 | Bredno et al. |
| 2014/0211910 A1* | 7/2014 | Subramanian ......... A61B 6/027 378/5 |
| 2015/0042844 A1 | 2/2015 | Shu et al. |
| 2015/0048826 A1 | 2/2015 | Hori et al. |
| 2015/0313565 A1 | 11/2015 | Matsuda |

FOREIGN PATENT DOCUMENTS

| | | |
|---|---|---|
| CN | 104706371 A | 6/2015 |
| JP | H05154142 | 6/1993 |
| JP | 2007125129 A | 5/2007 |
| JP | 2010252951 A | 11/2010 |
| JP | 5102953 B2 | 12/2012 |
| WO | 03028554 A1 | 4/2003 |

OTHER PUBLICATIONS

Written Opinion in PCT/CN2016/099069 dated Nov. 29, 2016, 12 pages.

\* cited by examiner

SYSTEM AND METHOD FOR COMPUTED TOMOGRAPHY

CROSS-REFERENCE TO RELATED APPLICATIONS

This application is a continuation of U.S. patent application Ser. No. 15/638,610 filed on Jun. 30, 2017, which is a continuation of International Application No. PCT/CN2016/099069, filed on Sep. 14, 2016, which claims priority of Chinese Patent Application No. 201510598603.0 filed on Sep. 18, 2015, and Chinese Patent Application No. 201510639797.4 filed on Sep. 30, 2015. Each of the above-referenced applications is expressly incorporated herein by reference to their entireties.

TECHNICAL FIELD

The present disclosure relates to computed tomography (CT) imaging technical field, and more particularly, to a method and system for correction of computed tomography imaging.

BACKGROUND

During the process of computed tomography imaging, artifacts are inevitable. In order to eliminate or weaken these artifacts, scan data or reconstructed images may be processed using artifacts correction. The artifacts may be caused by many reasons such as different gains of pixel units of a detector and a variation over time of the detector gain. In addition, the anomalies in the imaging process may also cause artifacts for example, the detector temperature exceeding the applied temperature of the air correction table, and the sudden emergence of damaged channels in the imaging process, etc. In order to further reduce artifacts and improve image quality, there is a need for a system and method for computed tomography imaging, in which real-time judgment and reminders of the artifacts and quick updating of the correction parameters may be achieved during the imaging process.

SUMMARY

According to an aspect of the present disclosure, a method for computed tomography imaging is provided. The method for computed tomography imaging may include: acquiring a first air correction table corresponding to a first temperature of the detector, the first air correction table comprises air correction parameters of at least one set of scan protocols at the first temperature, and the at least one set of scan protocols includes a first set of scan protocols; acquiring second temperature of the detector; and determining a second air correction table corresponding to the second temperature according to the second temperature and the first air correction table, the second air correction table comprises air correction parameters of at least one set of scan protocols at the second temperature.

According to some embodiments of the present disclosure, using the second temperature and the first air correction table to determine the second air correction table corresponding to the second temperature may include: determining that the second temperature is higher than the first temperature to acquire a first determination result; and determining the second air correction table corresponding to the second temperature according to the second temperature and the first air correction table, basing on the first determination result.

According to some embodiments of the present disclosure, the method for computed tomography imaging may further include: acquiring original data corresponding to the second temperature, the original data may include original scanned data or original images acquired from the original scanned data, the original data may include artifacts; and correcting the artifacts of the original data according to the second air correction table.

According to some embodiments of the present disclosure, the method for computed tomography imaging may further include: determining that the second temperature is equal to the first temperature to acquire a second determination results; and correcting the artifacts of the original data according to the first air correction table, basing on the second determination result.

According to some embodiments of the present disclosure, the artifacts may include ring artifacts or arc artifacts.

According to some embodiments of the present disclosure, the method for computed tomography imaging may further include: determining that the second temperature is higher than the first temperature to acquire a third determination result; and prompting a user according to the third determination result.

According to some embodiments of the present disclosure, using the second temperature and the first air correction table to determine the second air correction table corresponding to the second temperature may include: implementing air scanning at the second temperature, the air scanning includes implementing air scanning based on the first set of the scan protocols; acquiring air correction parameters of the first set of scan protocols at the second temperature according to the air scanning; and determining the second air correction table corresponding to the second temperature according to the air correction parameters of the first air correction table and the first set of scan protocols at the second temperature.

According to some embodiments of the present disclosure, the at least one set of scan protocols may include a second set of scan protocols. Using the air correction parameters of the first air correction table and the first set of scan protocols at the second temperature to determine the second air correction table corresponding to the second temperature may include: acquiring the air correction parameters of the first set of scan protocols at the first temperature; acquiring a D-value between the air correction parameters of the first set of scan protocols at the second temperature and the air correction parameters of the first set of scan protocols at the first temperature; acquiring the air correction parameters of the second set of scan protocols at the first temperature; and determining the air correction parameters of the second set of scan protocols at the second temperature according to the air correction parameters of the D-value and the second set of scan protocols at the first temperature.

According to another aspect of the present disclosure, a method for computed tomography imaging is provided. The method may include: a) acquiring original data, the original data includes the original scanned data or the original images acquired from the original scanned data; b) preprocessing the original data to get a preprocessing result; c) acquiring the intensity of the artifacts according to the preprocessing result; and d) updating the correction parameters according to the intensity of the artifacts.

According to some embodiments of the present disclosure, the artifact may include ring artifact or arc artifact.

According to some embodiments of the present disclosure, updating the correction parameters according to the intensity of the artifacts may include: determining that the intensity of the artifacts is equal to or larger than a first threshold to acquire a forth determination result; and updating the correction parameters according to the forth determination result.

According to some embodiments of the present disclosure, preprocessing the original data to get a preprocessing result may include: acquiring the original correction parameters; and correcting the artifacts of the original data according to the original correction parameters to get first correction data.

According to some embodiments of the present disclosure, the correction parameters may include the air correction table or a marked damaged channels.

According to some embodiments of the present disclosure, updating the correction parameters according to the intensity of the artifacts may include: determining the types of the correction parameters that need to be updated according to the intensity of the artifacts.

According to some embodiments of the present disclosure, determining the types of the correction parameters that need to be updated according to the intensity of the artifacts may include: acquiring the mean value of the scanned data of the channels at a plurality of angles of view corresponding to the artifact; determining that the mean value is larger than or equal to a second threshold, or is less than or equal to a third threshold, to get a fifth determination result; and marking the damaged channels according to the fifth determination result; determining that the mean value is less than the second threshold and is larger than the third threshold to get the sixth determination result; acquiring the deviation of the scanned data between the channels of the artifact and their adjacent channels according the sixth determination result; determining that the deviation is larger or equal to a fourth threshold to get a seventh determination result; marking the damaged channels according to seventh determination result; and determining that the deviation is less than the fourth threshold to get a eighth determination result; and updating the air correction parameters according to the eighth determination result.

According to some embodiments of the present disclosure, the method for computed tomography imaging may further include: e) correcting the artifacts of original data according to the updated correction parameters to get second correction data; and f) acquiring images according to the second correction data.

According to some embodiments of the present disclosure, the method for computed tomography imaging may further include: g) determining that the intensity of the artifacts is less than the first threshold to get a ninth determination result; and h) acquiring images according to the original data or the preprocessing result based on the ninth determination result.

According to some embodiments of the present disclosure, the method for computed tomography imaging may further include: scanning the N objects, implementing step a) to step h) for the M-th object, implementing step a), b) and h) for the other N-1 objects, M, N are integer, M is less or equal to N, and M is larger than 1.

According to some embodiments of the present disclosure, the method for computed tomography imaging may further include: determining that the intensity of the artifacts is larger than or equal to the first threshold to get tenth determination result; and prompting a user according to the tenth determination result.

According to an aspect of the present disclosure, a method for computed tomography imaging is provided. The method may include: acquiring original data which may include original scanned data or original images acquired from the original scanned data; preprocessing the original data to get the preprocessing result; acquiring the intensity of the artifacts according to the preprocessing result; and updating the damaged channels or air correction table according to the intensity of the artifacts, wherein updating the air correction table includes: acquiring the first air correction table corresponding to the first temperature of the detector, the first air correction table includes the air correction parameters of at least one set of scan protocols at the first temperature, the at least one set of scan protocols include the first scan protocol; acquiring the real-time temperature of the detector; and acquiring a second air correction table corresponding to the real-time temperature according to the real-time temperature and the first air correction table, the second air correction table includes the air correction parameters of at least one set of scan protocols at the real-time temperature.

According to an aspect of the present disclosure, a system for computed tomography imaging is provided. The system may include: an updating unit. The updating unit may update the correction parameters. The updating unit may include: correction table acquiring sub-unit, temperature acquiring sub-unit, and correction table updating sub-unit. The correction table acquiring sub-unit may acquire the first air correction table, which may include the air correction parameters of at least one set of scan protocols at the first temperature, corresponding to the first temperature of the detector. The at least one set of scan protocols may include the first scan protocol. The temperature acquiring sub-unit may acquire the second temperature of the detector. The correction table updating sub-unit may determine the second air correction parameters corresponding to the second temperature according to the second temperature and the first air correction table. The second air correction table may include air correction parameters of the at least one set of scan protocols at the second temperature.

According to another aspect of the present disclosure, a system for computed tomography imaging is provided. The system may include: original data acquiring unit and updating unit. The original data acquiring unit may acquire original data. The original data may include original scanned data or original images acquired from the original scanned data. The updating unit may update correction parameters. The updating unit may include: preprocessing sub-unit, artifacts information extracting sub-unit, and correction parameters updating sub-unit. The preprocessing sub-unit may preprocess the original data to get the preprocessing result. The artifacts information extracting sub-unit may acquire the intensity of the artifacts according to the preprocessing result. The correction parameters updating sub-unit may update correction parameters according to the intensity of the artifacts.

Part of additional features of the present disclosure may be described in the following description. Part of additional features of the present disclosure is obvious for those skilled in the field upon examination of the following and the accompanying drawings or may be learned by production or operation of the embodiments. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
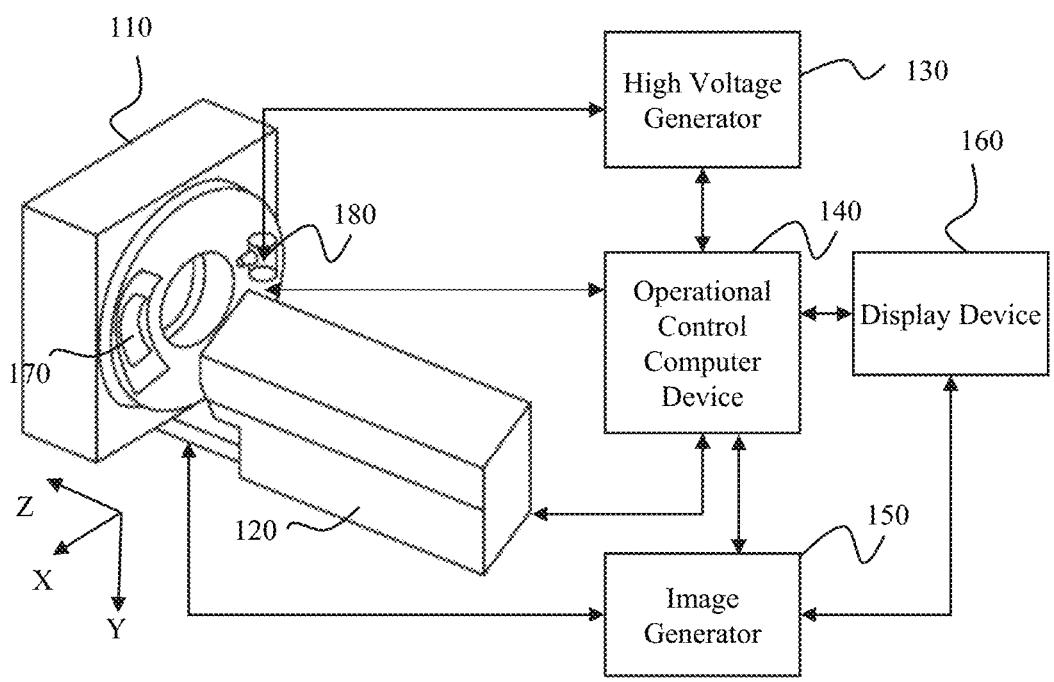
FIG. 1 is a block diagram of an exemplary imaging system 100 according to some embodiments of the present disclosure.

In the following detailed description, numerous specific details of the drawings appeared in the embodiments are set forth by way of example in order to provide a thorough understanding of the technical scheme of the present disclosure. Obviously, the drawings of following description are only some examples or embodiments of the present disclosure, and it should be apparent to those skilled in the art that the present disclosure may be applied to other similar situations according to these drawings without creative labor. It should be understood that these embodiments are presented only to enable those technicians skilled in the art to better understand and implement the present disclosure, rather than limiting the scope of the present disclosure in any way. The same label in the drawings represents the same structure or operation unless it is obvious in language or gets an additional explanation.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in the present disclosure, specify the presence of integers, devices, behaviors, stated features, steps, elements, operations, and/or components, but do not exclude the presence or addition of one or more other integers, devices, behaviors, features, steps, elements, operations, components, and/or groups thereof, the method or device may include other steps or elements.

Although the present disclosure makes various references to certain modules in the system based on the embodiments of the present disclosure, however, any number of different modules may be used and run on the client and/or server. The module s are illustrative only, and different aspects of the system and method may be used in different modules.

The flow chart of the present disclosure is used to illustrate the operation performed by the system according to the embodiments of the present disclosure. It should be understood that the preceding or following operations are not necessary performed exactly in order. On the contrary, the various steps may also be handled in inverted order or at the same time. Meanwhile, other operations may be added to these processes, or one or more of these steps may be removed.

FIG. 1 is a block diagram of an exemplary imaging system 100 according to some embodiments of the present disclosure. In some embodiments, the imaging system 100 may scan a given target to obtain scanned data and generate a related image. In some embodiments, the imaging system 100 may further process the scanned data or the generated image. For example, the imaging system 100 may be used to perform artifacts correction of the scanned data or the generated image. In some embodiments, the imaging system 100 may be a device or a group of devices. Specifically, the imaging system 100 may be a medical imaging system, for example, a Positron Emission Tomography (PET) device, a Single Photon Emission Computed Tomography (SPECT) device, a Computed Tomography (CT) device, a Magnetic Resonance Imaging (MRI) device, etc. Further, the medical imaging system may be used alone or in combination. For example, a PET-CT device, a PET-MRI device or a SPECT-MRI device.

In some embodiments, the imaging system 100 may include a scanner that scans a given target and obtains information associated with the given target (e.g., scanned data). Further, the imaging system 100 may include a radioactive scanning device. The radioactive scanning device may include a radioactive scanning source. The radioactive source may emit radioactive rays to a given target. The radioactive rays may include particle rays, photon rays, or a combination thereof. The particle ray may include neutrons, protons, electrons, a μ medium, a heavy ion, etc., or a combination thereof. The photon rays may include X-rays, gamma rays, alpha rays, beta rays, ultraviolet rays, lasers, etc., or a combination thereof. For example, the photon rays may be X-rays, and the system 100 may include at least one of a computed tomography system (CT), a digital X-ray imaging system (DR), and a multi-modal medical imaging system, etc. Further, in some embodiments, a multi-modal medical imaging system may include at least one of the PET-CT system, the SPECT-MRI system, and the like.

In some embodiments, the imaging system 100 may include a cavity 110, a bedstead 120, a high voltage generator 130, an operation computer device 140, an image generator 150, and a display device 160. The cavity 110 may accommodate one or more components for generating and detecting radioactive rays. In some embodiments, the cavity 110 may accommodate a radiation generator 180 and a detector 170. The radiation generator 180 may emit radioactive rays. In some embodiments, the radioactive rays may be emitted to a detected subject that is placed in the cavity 110, and received by the detector 170. For example, the radiation generator 180 may be an X-ray tube. The X-ray tube may emit X-rays that pass through a detected subject that is placed inside the cavity 110, and received by the detector 170. In some embodiments, the radioactive rays may be emitted to a detected subject that is placed in the cavity 110, and received by the detector 170 after being reflected by the detected subject. In some embodiments, the detector 170 may be a circular detector, a square detector, an arc detector, or a combination thereof. The rotation angle of the arc detector may be between 0 degree and 360 degrees. In some embodiments, the rotation angle of the arc detector may be fixed. In some embodiments, the rotation angle of the arc detector may be adjusted as required. For example, it may be adjusted according to the resolution of the image, the size of the image, the sensitivity of the detector, or the stability of the detector. In some embodiments, the detector 170 may be a one-dimensional detector, a two-dimensional detector, or a three-dimensional detector. In some embodiments, the detector 170 and the radiation generator 180 may rotate around the Z axis. In some embodiments, the detector 170 may be connected to one or more sensors, which may be used to detect one or more parameters of the detector 170 (e.g., a detector temperature). In some embodiments, the sensor may include a temperature sensor, or a gravity sensor, etc.

The bedstead 120 may support the detected subject (for example, a patient to be detected). In some embodiments, the bedstead 120 may move inside the cavity 110 in the process of detection. As shown in FIG. 1, the bedstead 120 may move along the Z axis in the detection process. The patient may be supine, prone, head in front or foot in front according to the requirement of the detection. In some embodiments, the bedstead 120 may move inside the cavity 110. The moving speed of the bedstead 120 may be constant or variable. The moving speed of the bedstead 120 may be related to the scanning time, and the scanning area, etc. In some embodiments, the moving speed of the bedstead 120 may be a default, a value which is set by a user (e.g., a doctor, an imaging technician), or a combination thereof. For example, the moving speed of the bedstead 120 may be default set by the system. When no value is set by the user, the bedstead 120 may move according to the system default. When the moving speed of the bedstead 120 is set by the user, the system default setting of the moving speed of the bedstead 120 may be ignored. Further, the bedstead 120 may move according to the moving speed set by the user. In some embodiments, the imaging system 100 may perform a helical scan. Specifically, the rotation of the detector 170 and the radiation generator 180 around Z axis, and the movement of the bedstead 120 along the Z axis may be performed at the same time in the process of spiral scanning. In some embodiments, the imaging system 100 may perform axial scanning. Specifically, the rotation of the detector 170 and the radiation generator 180 around Z axis, and the movement of the bedstead 120 along the Z axis may not be performed at the same time in the process of axial scanning. For example, when the detector 170 and the radiation generator 180 are rotating around the Z axis, the bedstead 120 may be stationary.

The high voltage generator 130 may generate high voltage or high current. In some embodiments, the generated high voltage or high current may be transmitted to the radiation generator 180. The generated high voltage may be 80 kV-140 kV, 75 Kv-150 kV or 120 kV-140 kV. The generated current may be 20 mA-500 mA.

The operational control computer device 140 may connect with the cavity 110, the radiation generator 180, the detector 170, the high voltage generator 130, the bedstead 120, the image generator 150, and/or the display device 160. The above mentioned devices may be connected directly or indirectly. In some embodiments, the operational control computer device 140 may control the radiation generator 180 and the detector 170 to rotate around the Z axis. In some embodiments, the operational control computer device 140 may control the 120 to move along the Z axis. In some embodiments, the operational control computer device 140 may control the cavity 110 to rotate to a certain position. The location may be a default set by the system, or may be set by a user (e.g., a doctor, an imaging technician, etc.). In some embodiments, the operational control computer device 140 may control the high voltage generator 130. For example, the operational control computer device 140 may control the intensity of voltage or current generated by the high voltage generator 130. In some embodiments, the operational control computer device 140 may control the display device 160. For example, the operational control computer device 140 may control the parameters associated with the display. The parameters may include display size, display scale, display order, display quantity, etc. For example, the whole or a part of a display image may be controlled. As another example, an image may be divided into several sub images (e.g., the head sub-graph, neck sub-graph, lower limb sub-graph, etc.), and these sub images may be display at the same time or one by one. As still another example, the image may be zoomed in or out.

The image generator 150 may generate images. In some embodiments, the image generator 150 may perform the operations of image preprocessing, image reconstruction, and/or artifacts correction, etc. The image generator 150 may connect with the detector 170, the operating control computer device 140, the display device 160 and/or an external data source (not shown in FIG. 1). In some embodiments, the image generator 150 may receive data from the detector 170 or the external data source, and generate an image based on the received data. The external data source may be hard disk, floppy disk, random access memory (RAM), dynamic random access memory (DRAM), static random access memory (SRAM), bubble memory, thin film memory, magnetic plating line memory, phase change memory, flash memory, cloud disk, or the like, or any combination thereof. In some embodiments, the image generator 150 may transmit the generated image to the display device 160 for displaying.

The display device 160 may display the received scanned data or image. The display device 160 may be connected to the operational control computer device 140 and the image generator 150. In some embodiments, the display device 160 may display an image generated by the image generator 150. In some embodiments, the display device 160 may display a prompt for a user (e.g., a doctor, an imaging technician, etc.). For example, when the image generator 150 determines that it is necessary to update the correction parameters (e.g., an air correction table, a marked damaged channel, etc.), the user may be prompted whether to update the correction parameters by the display device 160. The correction parameters described herein may refer to the parameters used by the image generator 150 to perform artifacts correction to scanned data or images. The display device 160 may prompt the user in the form of a dialog box, a hint tone, a voice, or a combination thereof. The user may choose whether to reply the prompt, and the method of replying may include at least one of manual input, voice input, etc. For example, when the user is prompted to update the correction parameters, the user may click "confirm" on the display device 160, which means the user chooses to update the correction parameters; otherwise, the user may click "Cancel" on the display device 160, which means the user chooses not to update the correction parameters. In some embodiments, the display device 160 may display the kind of correction parameters that need to be updated (e.g., an air correction table, a marked bad channel, etc.). In some embodiments, the display device 160 may send commands to the image generator 150 and/or the operational control computer device 140. For example, the user may set the imaging parameters by the display device 160, which may be sent to the operational control computer device 140. The imaging parameters may include scanning protocol and image reconstruction parameters, etc. The scanning protocol may include one or more scanning parameters, for example, a scanning time, scanning target location information, a frame rotation speed, a voltage/current intensity, etc. Different detected subjects may correspond to different scan protocols. The image reconstruction parameters may include at least one of the reconstructed field of view, the reconstruction matrix, and the reconstruction algorithm, etc.

It should be noted that the above description of the imaging system 100 is merely provided for purpose of illustration, and not intended limit the scope of the application in said embodiments. It is understood for persons having ordinary skills in the art, multiple variations and modifications of the method and system in application field and details may be made under the teachings of the present disclosure based on the mechanism. They may implement any combination of modules, or construct subsystems connected with other modules. For example, imaging system 100 may also include an external device (e.g., a database, a terminal, etc.) associated with the imaging system 100.

Figure 2:
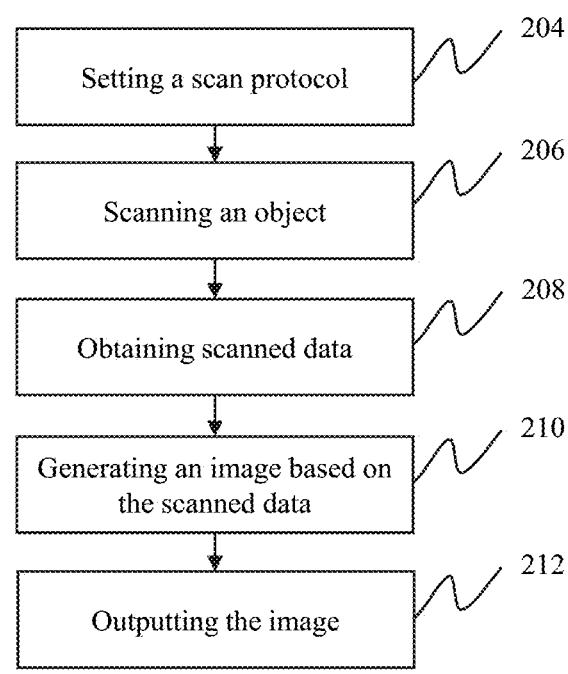
FIG. 2 is a flow chart of an exemplary process for generating images according to some embodiments of the present disclosure.

FIG. 2 is a flow chart of an exemplary process for generating images according to some embodiments of the present disclosure. In step 204, the scan protocol may be set. The setting of the scan protocol may be implemented by the operational control computer device 140. In some embodiments, the scan protocol may include at least one of a scanning time, scanning target location information, a position of the frame, a rotation speed of the frame, and a voltage/current intensity. For example, the bedstead 120 may rotate to a certain position. As another example, the cavity 110 may be moved to a certain position. In some embodiments, the certain position may be a system default, set by a user (e.g., a doctor, an imaging technician, etc.), or a combination thereof. In some embodiments, the set position is different depending on the different objects. In some embodiments, an object may be a whole or a portion of the detected subject. The detected subject may include human body, animal, non-biological object, etc. For example, the detected subject may include organs, tissues, lesions, tumors, or any combinations thereof. For example, the object may be the head, chest, abdomen, heart, liver, upper limbs, lower limbs, spine, bone, blood vessels, or the like, or any combination thereof.

In step 206, the object may be scanned. In step 208, the scanned data of the object may be obtained. The scanning process and the process of obtaining the scanned data may be accomplished together by the radiation generator 180 and the detector 170. In some embodiments, the radioactive rays may be received by the detector 170 after being absorbed by the object. In some embodiments, the radioactive rays may be reflected from the object to the detector 170 and received by the detector 170. In some embodiments, the scanned data may be obtained wholly or partially from an external data source. In some embodiments, the scanned data may be processed. The processing of the scanned data may include the noise reduction of the scanned data, artifacts correction, etc.

In step 210, images may be generated based on the scanned data. In some embodiments, step 210 may be implemented by the image generator 150. The generated images may include CT images, MRI images, PET images, or any combination thereof. For example, the CT images may be generated by using the reconstruction algorithm. In some embodiments, the generated images may include two-dimensional images or three-dimensional images. In some embodiments, the generated images may also be processed. The image processing may include image noise reduction, gray level normalization, image rotation, scale adjustment, partial occlusion removal (e.g., removal of glasses), artifacts correction, etc.

In step 212, the images may be output. In some embodiments, the images may be displayed by the display device 160. In some embodiments, the images may be transmitted to any external device associated with the imaging system 100, such as a database, a terminal, etc.

It should be noted that the above description of the imaging system 100 is merely provided for purpose of illustration, and not intended limit the scope of the application in said embodiments. It is understood for persons having ordinary skills in the art, multiple variations and modifications of the method and system in application field and details may be made under the teachings of the present disclosure based on the mechanism. They may combine or exchange each step arbitrarily. For example, additional options or processing requirements may be added between step 208 of acquiring scanned data and step 210 of generating images. For example, the scanned data may be stored for backups. Similarly, the step of storage backups may be added to any two steps in the flowchart.

Figure 3:
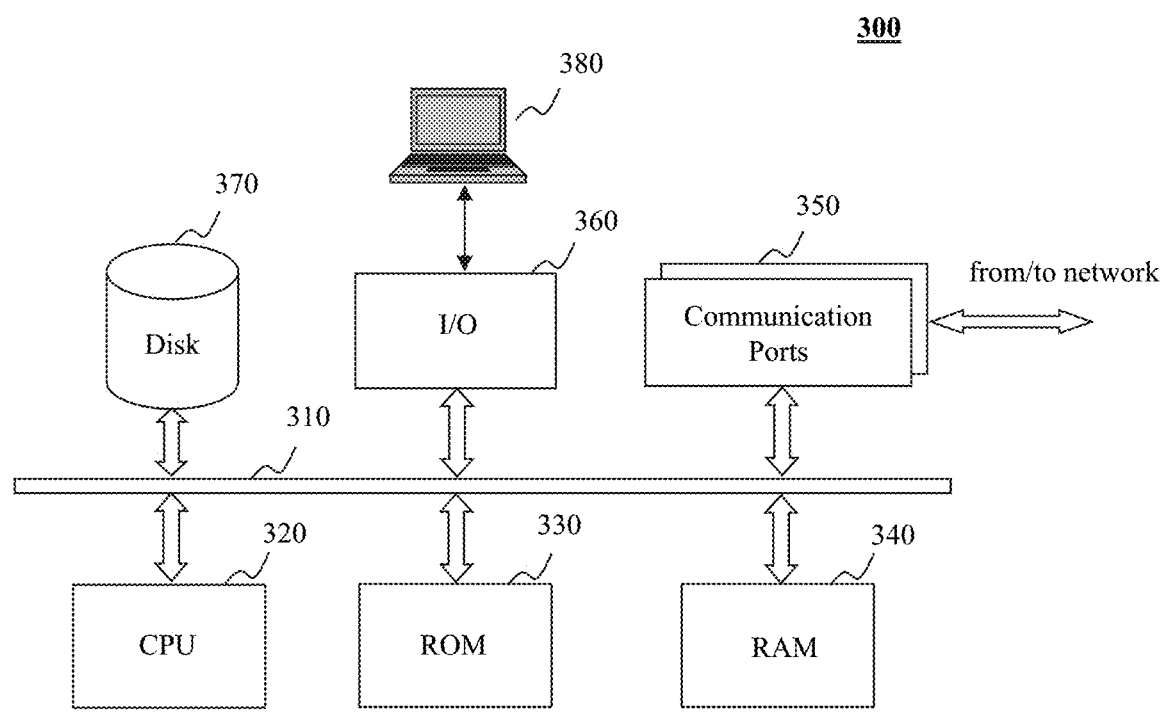
FIG. 3 is a schematic diagram illustrating an exemplary computer on which specific systems may be implemented according to some embodiments of the present disclosure.

FIG. 3 is a schematic diagram illustrating an exemplary compute on which specific systems may be implemented according to some embodiments of the present disclosure. The computer may be a general-purpose computer or a computer with a specific purpose. Two kind of computers may both be configured to implement a particular system in the embodiment. The computer 300 may be configured to be any component in which the information is required for imaging in the imaging system 100 of the present disclosure. For example, the image generator 150 may be implemented by a computer such as the computer 300 through its hardware, software, firmware, and their combination. For convenience, there is only one computer in FIG. 3, but the computer implementation function of the required information for imaging in the imaging system 100, which is described in the embodiment, may be set in a distributed manner, implemented by a group of similar platform, and disperse the processing load of the system.

The computer 300 may include a communication port 350, which may be connected to a network for data communication. The computer 300 may also include a central processing unit (CPU) unit 320 for executing the program instructions, consisting of one or more processors. The illustrated computer platform includes an internal communication bus 310, different forms of the program storage unit and a data storage unit, such as a hard disk 370, read-only memory (ROM) 330, random access memory (RAM) 340, various kinds of data files which may be configured for computer processing and/or communication, and feasible program instructions executed by CPU. The computer 300 may also include an input/output component 360 to support the input/output data flow between the computer and other components (such as the user interface 380). Computer 300 may also receive programs and data through the communication network.

Figure 4:
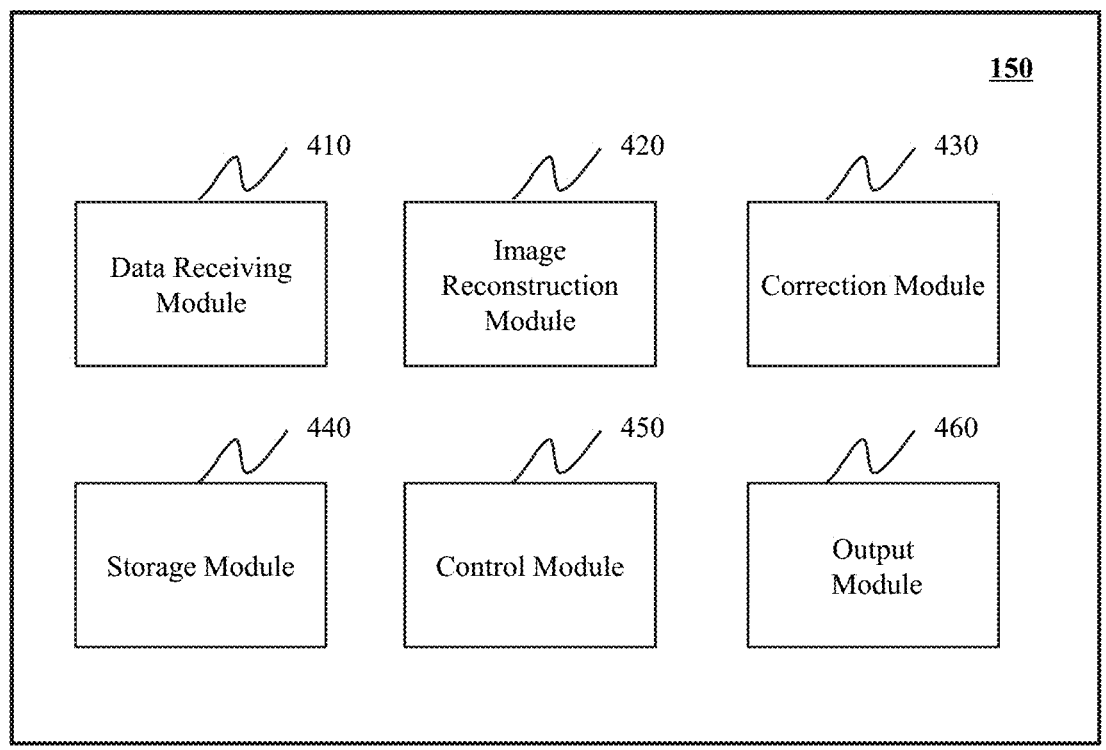
FIG. 4 is a block diagram of an exemplary image generator 150 according to some embodiments of the present disclosure.

FIG. 4 is a block diagram of an exemplary image generator 150 according to some embodiments of the present disclosure. The image generator 150 may include a data receiving module 410, an image reconstruction module 420, a correction module 430, a storage module 440, a controlling module 450, and an output module 460. In some embodiments, the data receiving module 410 may be implemented by a computer such as the computer 300 through an input/output component 360 and/or a communication port 350. The output module 460 may be implemented by a computer such as the computer 300 through an input/output component 360 and/or a communication port 350. The image reconstruction module 420, the correction module 430 and/or the control module 450 may be implemented by a computer such as the computer 300 through the CPU 320 and/or the hard disk 370. The memory module 440 may be implemented by a computer such as the computer 300 through the ROM 330 and/or the RAM 340.

The data receiving module 410 may receive data related to the object or data related to the system. The data received by the data receiving module 410 may include the basic information of the object (e.g., name, age, gender, height, weight, history etc.), scanning protocols, scanned data, images, detector temperatures, correction parameters, etc. The correction parameters may be used to correct scanned data or images. In some embodiments, the scanned data may be collected and transmitted by the detector 170 to the data receiving module 410. In some embodiments, the scanned data is collected by the detector 170, which may then be transmitted to any of the storage devices associated with the system 100, and then transmitted to the data receiving module 410 from the storage devices. In some embodiments, the data receiving module 410 may receive a scan protocol from the operational control computer device 140. In some embodiments, the data receiving module 410 may receive the basic information of the object from any one of the storage devices associated with the system 100. In some embodiments, the data receiving module 410 may obtain the detector temperature from the detector 170. In some embodiments, the user (for example, a doctor, an imaging technician, etc.) may set the detector temperature by the display device 160 or an external equipment associated with the imaging system 100 (e.g., a terminal, etc.), then transmit the detector temperature to the operational control computer device 140. The data receiving module 410 may obtain the detector temperature from the operational control computer device 140. In some embodiments, the data receiving module 410 may obtain correction parameters from any storage device related to the system 100. In some embodiments, the data received by the data receiving module 410 may be stored in the memory module 440, or may be transmitted to other modules of the image generator 150 for processing. For example, the data receiving module 410 may receive the scanned data to the image reconstruction module 420 for image reconstruction. The scanned data may also be sent to the correction module 430 for artifacts correction. As another example, the data receiving module 410 may send the received correction parameters to the correction module 430 for artifacts correction, or the correction module 430 may update the correction parameters based on a specific condition. Further, for example, the data receiving module 410 may transmit the received scanning protocols, the detector temperatures and other parameters to the correction module 430, and the correction module 430 may update the correction parameters based on the scanning protocol and/or the detector temperatures.

The image reconstruction module 420 may generate images. In some embodiments, the image reconstruction module 420 may receive the original data from the data receiving module 410 or scanned data after artifacts correction from the correction module 430, and generate images based on the original scanned data or the scanned data after artifacts correction. In some embodiments, the image reconstruction module 420 may obtain the original scanned data from the memory module 440 or the scanned data after artifacts correction, and generate images. In some embodiments, the image reconstruction module 420 may process the generated images. The processing operation may include one or more of the filtering noise reduction, the normalization of the gray level, the horizontal rotation of the image, the adjustment of the scale size, and the removal of the partial occlusion (for example, the removal of glasses), etc. In some embodiments, the images generated by the image reconstruction module 420 may be transmitted to the output module 460 or stored in the memory module 440. In some embodiments, the image reconstruction module 420 may be optional. The image may be read from any storage devices related to the system 100 by the data receiving module 410.

The correction module 430 may perform the artifacts correction to the scanned data or the images according to the correction parameters, and/or update the correction parameters. The correction parameters may include an air correction table and/or a marked bad channel. In some embodiments, the correction module 430 may obtain scanned data from the data receiving module 410 or the memory module 440 and perform an artifacts correction to the scanned data. In some embodiments, the correction module 430 may obtain images from the image reconstruction module 420 or the memory module 440 and perform an artifacts correction to the images. In some embodiments, the correction module 430 may update the correction parameters. For example, the correction module 430 may update the air correction table according to the air scanning. The air scanning described here refers to the scanning of the imaging system 100 in the absence of an object. The air correction table may include correction parameters corresponding to one or more scan protocols obtained by air scanning (e.g., also referred to as "air correction parameters"). In some embodiments, the updated correction parameters may be stored in the memory module 440. In some embodiments, the correction module 430 may send instructions to the operational control computer device 140 through the output module 460. For example, the correction module 430 may send instructions of implementing air scanning to the operational control computer device 140 through the output module 460, and when the operational control computer device 140 receives an air scanning command, and then the operational control computer device 140 may control the scanner to implement the air scanning.

The storage module 440 may store data, images and/or related parameters. Data may be stored in various forms of data. For example, at least one of the values, signals, relevant information of a given target, commands, algorithms, programs, etc. For example, the scanned data, images and correction parameters may be stored in the storage module 440. In some embodiments, the storage module 440 may include fixed storage systems (e.g., disk), mobile storage system (e.g., the USB interface, the interfaces like FireWire port and/or the drivers like disk drive), etc. Specifically, in some embodiments, the storage module 440 may store the original scanned data, the original images, scanned data after artifacts correction (e.g., also referred to as the "pre-corrected scanned data"), images obtained by the scanned data after artifacts correction (e.g., also referred to as the "pre-corrected images"), images after artifacts correction (e.g., also referred to as "post-corrected images"), the original correction parameters, updated correction parameters, etc. The storage module 440 may be a temporary storage of data, i.e., the data may be transferred to the next data processing; the storage module 440 may be a long-term storage of the data, i.e., the final data processing result may be stored.

The control module 450 may control the data receiving module 410, the image reconstruction module 420, the correction module 430, the storage module 440, and/or the output module 460. In some embodiments, the control module 450 may control the receiving time and/or the path of data transmission of the data receiving module 410. In some embodiments, the control module 450 may control the data transmission rate and the data transmission mode (e.g., real-time transmission or delayed transmission), etc. In some embodiments, the control module 450 may control the image reconstruction module 420 for image reconstruction. For example, the control module 450 may select an algorithm for image reconstruction. In some embodiments, the control module 450 may control the correction module 430 for artifacts correction and/or updating correction parameters. In some embodiments, the control module 450 may receive commands from a user (e.g., a doctor, an imaging technician, etc.).

The output module 460 may output information. The information may include data, images, and/or related parameters. The information may be derived from the data receiving module 410, the image reconstruction module 420, the correction module 430, the storage module 440, and/or the control module 450. The information may have a plurality of presentation modes, including one or more of the audio, video, image, and text, etc. For example, the information may be broadcasted through a microphone, a loudspeaker, etc. As another example, the information may be displayed on the screen. In some embodiments, the information may be data of various forms, including the values, signals, relevant information of the given target, commands, algorithms, programs, or the like, or any combinations thereof. For example, the information may include the original images, the updated correction parameters, the scanned data after artifacts correction, and the images that have been corrected, etc. In some embodiments, the information may be outputted to any external device (e.g., a database, a terminal, etc.) associated with the imaging system 100. In some embodiments, the information may be displayed on any display device (e.g., a display device 160, a computer display screen, a mobile phone display screen, etc.).

In some embodiments, each module within the image generator 150 may include one or more general-purpose processors. The processor may include one or more of a programmable logic device (PLD), a special integrated circuit (ASIC), a microprocessor, a system on chip (SoC), a digital signal processor (DSP), etc. The two or more processors may be combined on a hardware device. The processor may implement data processing in a variety of ways, for example, through the combination of hardware, software or hardware-software. For example, the image generator 150 may be implemented by a computer such as the computer 300 through its hardware, software, firmware, or a combination thereof.

It should be noted that the above description of the image generator 150 is merely provided for purpose of illustration, and should not be considered as the only viable embodiment. It is obvious for persons having ordinary skills in the art, multiple variations and modifications of the method and system in application field and details may be made under the teachings of the present disclosure based on the mechanism, but these variations and modifications are still in the scope of the above description. For example, each module in the image generator 150 may be added with a storage unit for storing intermediate data or processing results generated during the operation of each module. For example, one or more modules may be integrated in the same module, to achieve the function of one or more modules. As another example, the data receiving module 410 and the output module 460 may be integrated in a module, while achieving the input/output function. Further, for example, the image generator 150 may omit the memory module 440, the intermediate data or the processing results generated during the operation of each module may be stored in the external data source through the output module 460.

Figure 5:
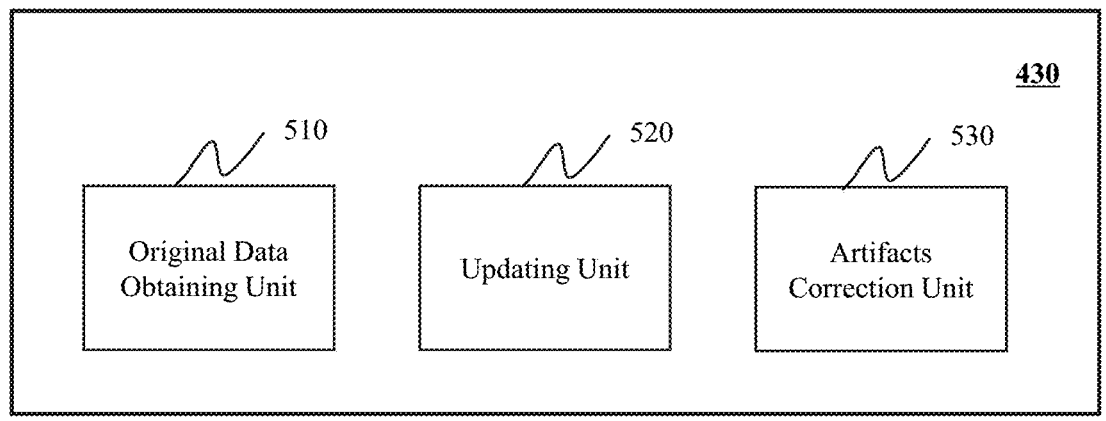
FIG. 5 is a block diagram of an exemplary correction module 430 according to some embodiments of the present disclosure.

FIG. 5 is a block diagram of an exemplary correction module 430 according to some embodiments of the present disclosure. As shown in FIG. 5, the correction module 430 may include an original data obtaining unit 510, an updating unit, and an artifacts correction unit 530.

The original data obtaining unit 510 may obtain the original data. The original data may include the original scanned data and/or the original images. The original scanned data or original images described herein may refer to the scanned data or images that have not been performed artifacts correction. In some embodiments, the original data obtaining unit 510 may obtain the original data from the data receiving module 410, the storage module 440, or the image reconstruction module 420. In some embodiments, the original data obtaining unit 510 may obtain the original data from any external device (e.g., a database, a terminal) associated with the imaging system 100. In some embodiments, the original data obtaining unit 510 may receive the original data inputted by a user (e.g., a doctor or an image technician).

The updating unit 520 may update correction parameters. The correction parameters may include an air correction table or a marked bad channel. The air correction table described herein may be obtained based on the results of an air scanning. The air scanning may refer to a scanning operation when there is no object in the imaging system 100. The air correction tables corresponding to different temperatures may be different. The air correction table corresponding to a certain temperature may include air correction parameters corresponding to at least one set of scanning protocols. In some embodiments, the correction parameters may be valid for a period of time (e.g., 3 months, 6 months, or 1 year, etc.). The correction parameters may be updated when the correction parameters are out of date or the original correction parameters are found not applicable in the operation of the imaging system 100. For example, when the detector temperature is found different from the temperature corresponding to the original correction parameters during the operation of imaging system 100, a user (e.g., a doctor, an imaging technician, etc.) may be prompted whether to update the correction parameters, or automatically update the correction parameters. In some embodiments, the updating unit 520 may send instructions to the operational control computer device 140 by the output module 460, and the operational control computer device may control the display device 160 and the external devices (e.g., terminals, etc.) associated with the imaging system 100, to prompt users (e.g., doctors, imaging technicians, etc.). For example, the updating unit 520 may prompt the user whether to update the correction parameters, and/or the types of the correction parameters to be updated.

The artifacts correction unit 530 may obtain the correction parameters, and/or perform the artifacts correction to the original data according to the obtained correction parameters. Artifacts may refer to various forms of shadows which may be seen in the images but not exist in the object. The cause of the artifacts may include the cause associated with the device or the cause associated with the object. In the case of CT imaging, artifacts associated with the device may include one or more of the artifacts associated with the system design, artifacts associated with the radiation generator, and artifacts associated with the detector. According to the form of artifacts, artifacts may include strip artifacts, shadow artifacts, arc or ring artifacts, etc. The cause of the strip artifacts may include one or more of the improper data sampling, partial volume effect, the motion of the object, a metal object, the beam hardening, the noise, the spiral scan, the mechanical failure, etc. The cause of the shadow artifacts may include one or more of partial volume effect, beam hardening, spiral scanning, scattering ray, extrafocal radiation, the incomplete of projection data, etc. The cause of the arc or ring artifacts may include one or more of the difference gains in pixel unit of detector, the change of the gain of the detector, the channel fault of the detector, etc. The gain of the detector described herein may refer to the increased intensity of current, voltage, or power of the detector.

In some embodiments, the artifacts correction unit 530 may obtain the original scanned data from the original data obtaining unit 510, and pre-correct the original scanned data (e.g., also referred to as "pretreatment") to generate pre-corrected scanned data. For example, the artifacts correction unit 530 may obtain the original images from the original data obtaining unit 510, and then post-correct the original images to generate the post-corrected images. Further, for example, the pre-corrected scanned data may be reconstructed to generate the pre-corrected images, and the artifacts correction unit 530 may post-correct the pre-corrected images to generate the post-corrected images. The pre-correction herein may refer to artifacts correction of the scanned data before the image reconstruction which may eliminate or reduce the artifacts. Post-correction may refer to artifacts correction of the image after reconstructing, which may eliminate or reduce artifacts. The pre-correction and post-correction may be performed independently or together in the imaging process. The pre-corrected scanned data herein may refer to the scanned data obtained from the pre-correction of the original scanned data. The pre-corrected image may be an image obtained by the image reconstruction of the pre-corrected scanned data. The post-corrected image may be an image obtained by the post-correction of the original image or the pre-corrected image.

Figure 6:
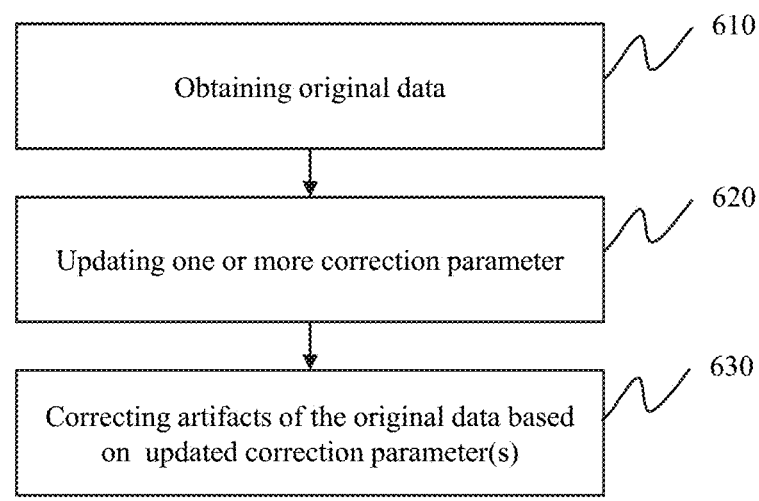
FIG. 6 is a flow chart of an exemplary process for correcting artifacts process according to some embodiments of the present disclosure.

FIG. 6 is a flow chart of an exemplary process for correcting artifacts according to some embodiments of the present disclosure. In step 610, the original data may be obtained. The process of obtaining the original data may be achieved by the original data obtaining unit 510. The original data may include the original scanned data and the original images. The original scanned data or original images described herein may refer to scanned data or images that have not been artifacts corrected. In step 620, the correction parameters may be updated. The process of updating the correction parameters may be achieved by the updating unit 520. In some embodiments, the correction parameters may be valid for a period of time (e.g., 3 months, 6 months, or 1 years, etc.), and when the imaging system 100 detects that the correction parameters have been expired, the correction parameters may be updated. For example, when an air correction table corresponding to a certain temperature is expired, a new air correction table corresponding to the temperature may be re-generated. In some embodiments, the imaging system 100 may be updated at a certain time interval (e.g., 1 months, 3 months, 6 months, 1 year, etc.). In some embodiments, the correction parameters may be updated in real time according to the condition of the imaging system 100. For example, when the detector temperature is different from the temperature corresponding to the air correction table in the operation process of the imaging system 100, the air correction table corresponding to the detector temperature may be updated and generated in real time, and the original data may be corrected according to the updated air correction table. For example, when the detector channel is damaged in the operation process of the imaging system 100, then the damaged channel may be marked, and the original data of the damaged channel may be corrected. As another example, when the air correction parameters of the air correction table corresponding to the set temperature is incorrect in the operation process of the imaging system 100, the air correction table corresponding to the set temperature may be updated.

In step 630, the original data may be corrected by the updated correction parameters. The artifacts correction may include a pre-correction and a post-correction. The pre-correction may be used to implement an artifacts correction of the scanned data before the image reconstruction, which may eliminate or reduce the artifacts. The post-correction may be used to implement an artifacts correction of the images after the image reconstruction, which may eliminate or reduce the artifacts. In the process of CT imaging, the pre-correction and the post-correction may be performed independently or together. In some embodiments, the artifacts correction of scanned data or images may be performed with different correction methods to eliminate or reduce the artifacts according to the cause of the artifacts. For example, for the artifacts caused by the detector gain, an air scanning may be performed to obtain an air correction table, which may be used to compensate for the gain of the detector based on the artifacts correction of the scanned data or image. As another example, for the artifacts caused by the damaged channel of the detector, the damaged channel of the detector may be marked, and the further artifacts correction may be performed to the scanned data or images acquired by the damaged channel. In some embodiments, two methods may be used to perform the artifacts correction to scanned data or images in combination with an air scanning and the marking of a damaged channel. In some embodiments, the steps of updating the correction parameters may occur in the process of pre-correction or in the process of post-correction.

In some embodiments, the artifacts correction process described in FIG. 6 may omit step 620, and perform the artifacts correction of the original data only on the basis of the original correction parameters. The artifacts correction process may perform the pre-correction or the post-correction independently or together. Specifically, for the process of implementing the pre-correction only, the artifacts correction of the original scanned data may be firstly performed according to the original correction parameters to generate scanned data of the pre-correction, then the reconstruction of scanned data of the pre-correction may be performed to generate pre-corrected images. For the process of implementing the post-correction only, firstly the original scanned data may be reconstructed to generate the original images, and then the original images may be corrected based on the original correction parameters to generate post-corrected images. For the process of implementing the pre-correction and the post-correction together, firstly the artifacts correction of the original scanned data may be performed according to the original correction parameters to generate pre-corrected scanned data, then the pre-corrected scanned data may be reconstructed to generate pre-corrected images, at last the pre-corrected images may be corrected according to the original correction parameters to generate post-corrected images. In some embodiments, the post-corrected images may include images generated by the artifacts correction of the pre-corrected images or the original images.

In some embodiments, the artifacts correction process described in FIG. 6 may further include a step of prompting a user, which may prompt the user to update the correction parameters. The process of prompting a user may be implemented by the updating unit 520. The method of prompting may include one or more of the display dialog box, the prompt tone, the voice prompt, etc.

It should be noted that the above description is merely provided for purpose of illustration, and should not be considered as the only viable embodiment. It is obvious for persons having ordinary skills in the art, multiple variations and modifications of the method and system in application field and details may be made under the teachings of the present disclosure based on the mechanism, but these variations and modifications are still in the scope of the above description. For example, step 620 may be performed before step 610, and when the temperature of the detector is different from the proper temperature of the air correction table, the air scanning may be implemented at the temperature of the detector to generate the air correction table corresponding to the temperature of the detector.

Figure 7:
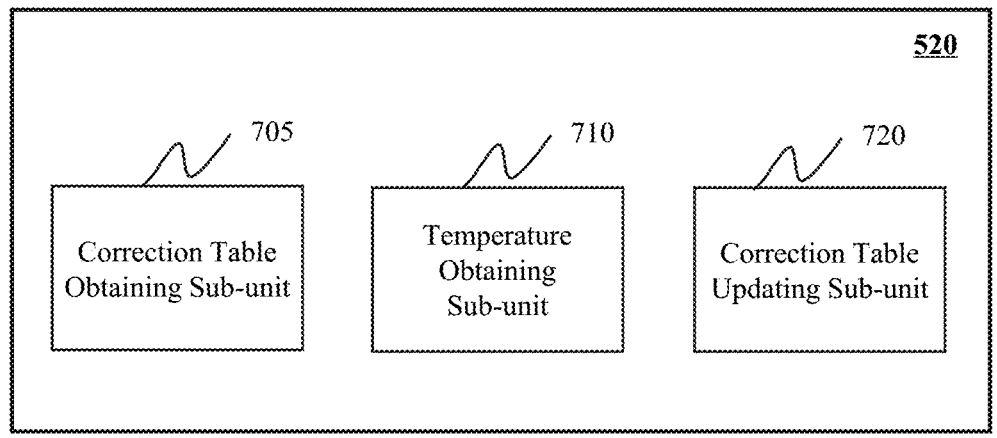
FIG. 7 is a block diagram of an exemplary updating unit 520 according to some embodiments of the present disclosure.

FIG. 7 is a block diagram of an exemplary updating unit 520 according to some embodiments of the present disclosure. As shown in FIG. 7, the updating unit 520 may include a correction table obtaining sub-unit 705, a temperature obtaining sub-unit 710, and a correction table updating sub-unit 720.

The correction table obtaining sub-unit 705 may obtain the first air correction table corresponding to the first temperature. The first temperature herein may refer to the normal operating temperature of the detector. In some embodiments, the first air correction table corresponding to the first temperature may include air correction parameters corresponding to at least one set of scan protocols at the first temperature. In some embodiments, the first air correction table may be stored in the storage module 440, and the correction table obtaining sub-unit 705 may obtain the first air correction table from the storage module 440. In some embodiments, the first air correction table may be stored in the external data source (not shown in the figures in the disclosure), and the correction table obtaining sub-unit 705 may obtain the first air correction table from the external data source through the data receiving module 410. In some embodiments, the correction table obtaining sub-unit 705 may be integrated in the artifacts correction unit 530. In some embodiments, the correction table obtaining sub-unit 705 may be optional, and the process of obtaining the first air correction table may be achieved by the artifacts correction unit 530.

The temperature obtaining sub-unit 710 may obtain the detector temperature (e.g., also referred to as "a second temperature of the detector"). In some embodiments, the detector temperature may include a real-time temperature or a set temperature of the detector. In some embodiments, the temperature obtaining sub-unit 710 may obtain the real-time temperature of the detector from the detector 170 via the data receiving module 410. In some embodiments, users (e.g., doctors, imaging technicians) may set the detector temperature through the display device 160 or the external device (e.g., a terminal, etc.) associated with the imaging system 100, and then send the set temperature to the operational control computer device 140. The temperature obtaining sub-unit 710 may obtain the set temperature from the operational control computer device 140 through the data receiving module 410.

The correction table updating unit 720 may update the air correction table. The updating air correction table described herein may refer to updating the air correction parameters corresponding to at least one set of scanning protocols in the first air correction table. In some embodiments, the correction table updating unit 720 may send instructions of an air scanning to the operational control computer device 140 through the output module 460, and the operational control computer device 140 may control the scanner to perform the air scanning. In some embodiments, the correction table updating unit 720 may send instructions of an air scanning to the operational control computer device 140 through the output module 460, and the operational control computer device 140 may control the display device 160 or the external device (e.g., terminal, etc.) associated with the imaging system 100 to prompt the users (e.g., doctors, imaging technicians, etc.). For example, when the first air correction table is not suitable (e.g., the detector temperature is different from the first temperature), the correction table updating unit 720 may send instructions to the operational control computer device 140 through the output module 460 to prompt the user whether to update the air correction table.

Figure 8:
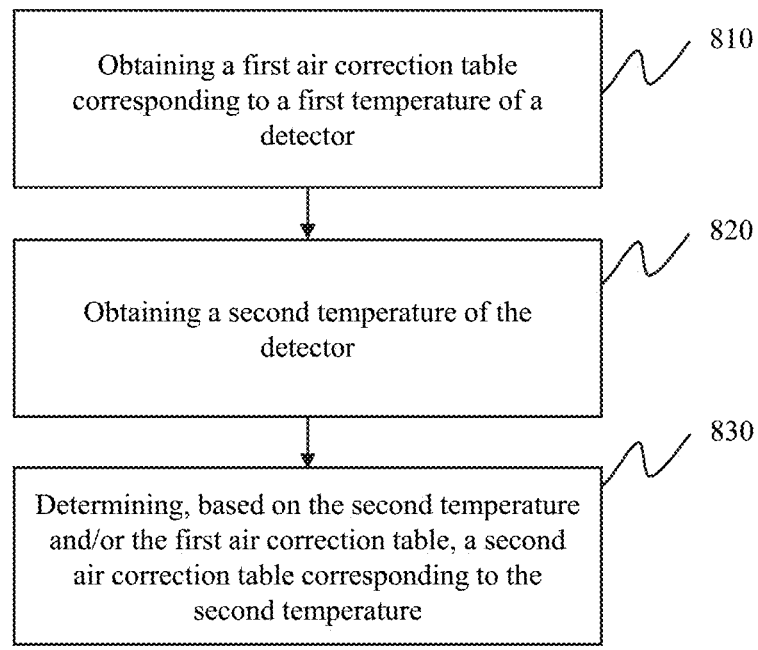
FIG. 8 is a flow chart of an exemplary process for updating air correction table according to some embodiments of the present disclosure.

FIG. 8 is a flow chart of an exemplary process for updating an air correction table according to some embodiments of the present disclosure. In step 810, the first air correction table corresponding to the first temperature of the detector may be obtained. The process of obtaining the first air correction table corresponding to the first temperature of the detector may be performed by the correction table obtaining sub-unit 705. In some embodiments, the first air correction table corresponding to the first temperature may include air correction parameters corresponding to at least one set of scan protocols at the first temperature. In some embodiments, the first temperature may be the normal operating temperature of the detector. In some embodiments, the first temperature may be any temperature. In some embodiments, the first air correction table may be stored in the storage module 440, and the correction table obtaining sub-unit 705 may obtain the first air correction table from the storage module 440. In some embodiments, the first air correction table may be stored in the external data source (not shown in the figures in the disclosure), the correction table obtaining sub-unit 705 may obtain the first air correction table from the external data source through the data receiving module 410. In some embodiments, when the correction table obtaining sub-unit 705 is integrated in the artifacts correction unit 530, or the updating unit 520 omits the correction table obtaining sub-unit 705, the process of obtaining the first air correction table may be performed by the artifacts correction unit 530.

In step 820, the second temperature of the detector may be obtained. The process of obtaining the detector second temperature may be performed by the temperature obtaining sub-unit 710. In some embodiments, the second temperature may be the real-time temperature of the detector, or the set temperature. In some embodiments, when the second temperature is a set temperature, the set temperature may be determined based on the user's settings. When the second temperature is the real-time temperature of the detector, the real-time temperature may be determined by one or more temperature sensors on the detector 170. For example, the average value of the measured temperature measured by temperature sensors may be taken as the real-time temperature of the detector. As another example, the average temperature measured by the temperature sensors for a period of time (e.g., 5 minutes, 10 minutes) may be used as the real-time temperature of the detector.

In step 830, the second air correction table corresponding to the second temperature may be obtained according to the second temperature of the detector and the first air correction table. The process of obtaining the second air correction table may be performed by the correction table updating unit 720. In some embodiments, the second air correction table corresponding to the second temperature may include air correction parameters corresponding to at least one set of scan protocols at the second temperature. In some embodiments, the air correction parameters of at least one set of scan protocols at the second temperature may be obtained firstly, then the second air correction table may be obtained according to the air correction parameters of at least one set of scan protocols at the second temperature and the first air correction table.

In some embodiments, the first temperature and the second temperature may be a temperature range or a specific temperature value. For example, the first temperature may be 39 degrees Celsius. In some embodiments, when the process of updating the air correction table is performed in the process of image reconstruction, the second temperature may be the real-time temperature of the detector. In some embodiments, the process of updating the air correction table may be performed at any time, and the second temperature may be an arbitrary temperature set by the system 100 or the user. For example, the system 100 may obtain a plurality of second air correction tables at a plurality of second temperatures according to the first air correction table.

Figure 9:
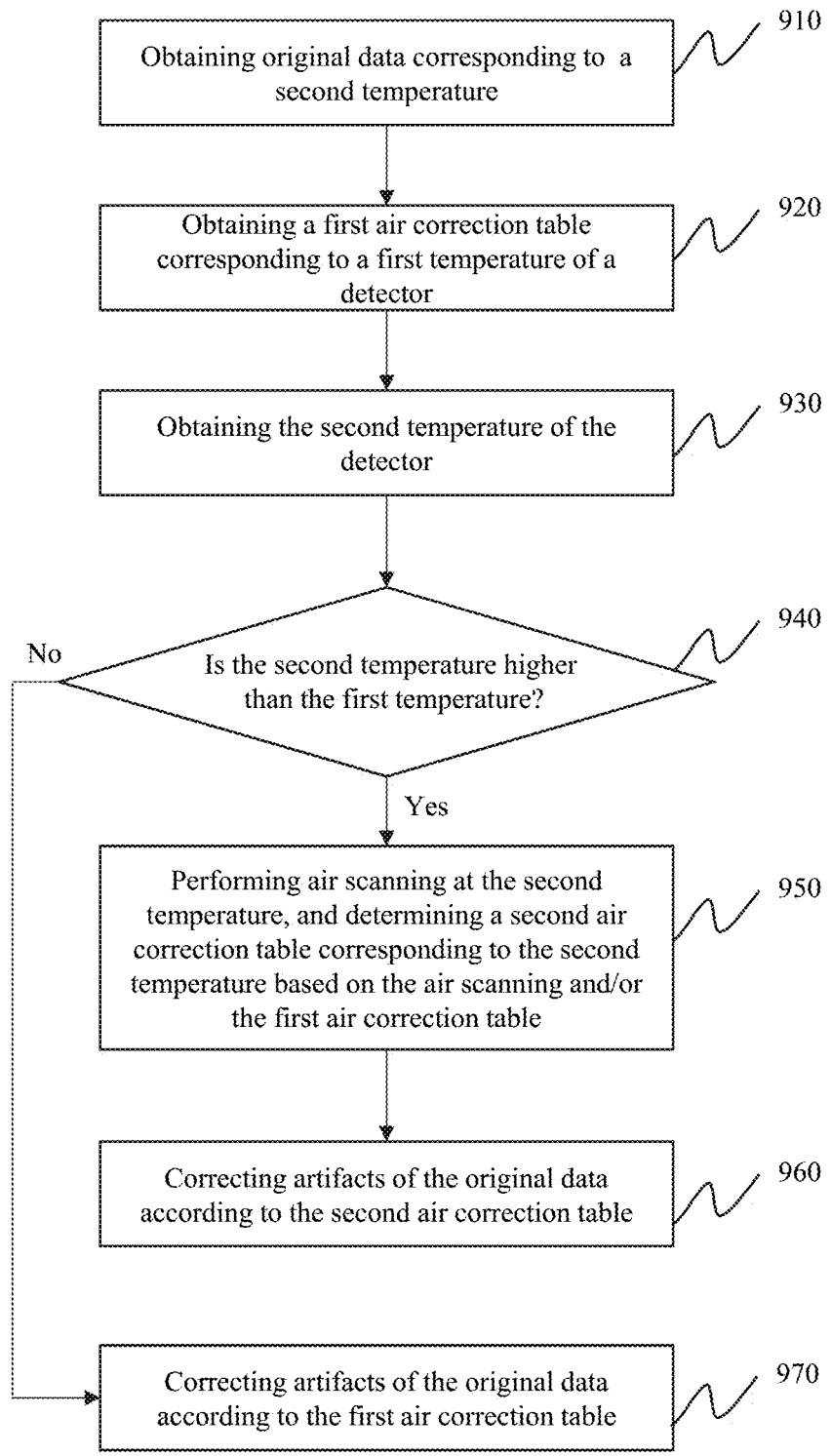
FIG. 9 is a flow chart of an exemplary process for correcting artifacts according to some embodiments of the present disclosure.

FIG. 9 is a flow chart of an exemplary process for correcting artifacts according to some embodiments of the present disclosure. In step 910, the original data corresponding to the second temperature may be obtained. The process of obtaining the original data corresponding to the second temperature may be performed by the original data obtaining unit 510. In step 920, the first air correction table corresponding to the first temperature of the detector may be obtained. The process of obtaining the first air correction table corresponding to the first temperature of the detector may be performed by the correction table obtaining sub-unit 705. In step 930, the second temperature of the detector may be obtained. The process of obtaining the detector second temperature may be performed by the temperature obtaining sub-unit 710. In step 940, it is required to determine whether the second temperature of the detector exceeds the first temperature. If the second temperature of the detector exceeds the first temperature, step 950 may be executed; if the second temperature of the detector does not exceed the first temperature, step 970 may be executed. The process of determining whether the second temperature of the detector exceeds the first temperature may be performed by the correcting table updating sub-unit 720.

In step 950, an air scanning may be implemented at the second temperature of the detector, and a second air correction table corresponding to the second temperature may be obtained according to the air scanning and the first air correction table. The process of obtaining the second air correction table corresponding to the second temperature may be performed by the correction table updating sub-unit 720. The air scanning described herein may refer to a scanning performed in the imaging system 100 without an object. In some embodiments, the correction table updating unit 720 may send instructions of the air scanning to the operational control computer device 140 through the output module 460, and the operational control computer device 140 may control the scanner to perform the air scanning.

Specifically, the correction reference value of the second temperature may be obtained based on the air scanning at the second temperature, and the second air correction table may be obtained based on the first air correction table and the correction reference value. For example, the air correction parameters of at least one set of scan protocols at the second temperature may be determined as the correction reference value, then a set of air correction parameters (the scan protocol corresponding to the air correction parameters herein is same as the scan protocol corresponding to the correction reference value) in the first air correction table corresponding to the correction reference value may be determined, the determination of a difference value between the air correction parameters and the correction reference value may be performed, and the air correction parameters of multiple scan protocols at the second temperature in the second air correction table may be determined according to the difference value. For example, the air scanning may be performed at the second temperature based on a scan protocol to obtain the scanned data of the second temperature, and the gain of detector 170 may be determined based on the scanned data, then the air correction parameters of the scan protocol at the second temperature may be determined based on the gain, at last the air correction parameters may be regarded as the correction reference value.

In some embodiments, the air correction parameters of two or more sets of scan protocols at the second temperature may be obtained through the air scanning. The air correction parameters of one set of the scan protocols may be selected as a correction reference value. Alternatively, the air correction parameters of multiple scan protocols at the second temperature in the second air correction table may be determined by the average value of the difference value which is determined between the air correction parameters of these scan protocols and the air correction parameters of the same scan protocols in the first air correction table.

For example of generating air correction parameters of a set of scan protocols at the second temperature, the correction reference value may be represented as $A_{new}$, the corresponding scan protocol may be represented as A, and the air correction parameters of the scan protocol A in the first air correction table may be represented as $A_{normal}$. The difference value between $A_{new}$ and $A_{normal}$ may be determined according to Equation (1):

$$\Delta A = A_{new} - A_{normal},\qquad(1)$$

where $\Delta A$ may represent the difference value between the correction reference value and the corresponding air correction parameters in the first air correction table.

For the first air correction table and the second air correction table, the difference value of the air correction parameters corresponding to different scan protocols may be same. The second air correction table may be determined based on Equation (2):

$$B_{new}=B_{normal}+\Delta A,$$

$$C_{new}=C_{normal}+\Delta A,$$

$$Z_{new}=Z_{normal}+\Delta A, \quad (2)$$

where $B_{new}$, $C_{new}$, and $Z_{new}$ may represent the air correction parameters of scan protocols of B, C and D in the second air correction table.

In some embodiments, the second air correction table may be obtained based on $A_{new}$, $B_{new}$, $C_{new}$, . . . , and $Z_{new}$.

In step 960, the original data may be corrected based on the second air correction table. The process of artifacts correction may be performed by the artifacts correction unit 530.

In some embodiments, the process described in FIG. 9 may also include prompting the user when the second temperature of the detector exceeds the first temperature. For example, the user may be prompted that the second temperature of the detector exceeds the first temperature, and/or whether to update the air correction table.

In some embodiments, step 910, step 920, and step 930 may be performed in any order. In some embodiments, a determination (step 940) on the detector temperature may be made at intervals in the operation process of the imaging system 100, and the determination may also be made before the scanning.

In some embodiments, the process described in FIG. 9 may be applied to update the air correction table in real-time in the operation process of imaging system 100, or to generate an air correction table corresponding to one or more temperatures. When the process is applied to generate an air correction table corresponding to a temperature, step 910, step 960, and step 970 may be omitted in the process described in FIG. 9.

In some embodiments, if the second temperature of the detector is higher than the first temperature in the operation process of the imaging system 100, firstly the air correction parameters corresponding to the scan protocol, which is set in the operation process of the imaging system 100, may be determined at the second temperature according to the air scanning, and then the original data may be corrected based on the air correction parameters. After the imaging process, the second air correction table corresponding to the second temperature may be generated according to the first air correction table and the air correction parameters corresponding to the scan protocol set in the operation process of the imaging system 100 at the second temperature.

In some embodiments, when the second temperature of the detector exceeds the first temperature, an operation may be performed to determine whether there is an air correction table corresponding to the second temperature in the storage module 440 or in the external data source. If there is an air correction table corresponding to the second temperature in the storage module 440 or in the external data source, the air correction table corresponding to the second temperature may be obtained from the storage module 440 or the external data source, and the original data may be corrected based on the air correction table corresponding to the second temperature; if there is no air correction table corresponding to the second temperature in the storage module 440 and the external data source, step 950 may be executed to implement an air scanning at the second temperature.

In some embodiments, when the second temperature of the detector is different from the first temperature (for example, the second temperature is lower than the first temperature), the second air correction table corresponding to the second temperature may be obtained based on the method described in FIG. 9 in the imaging system 100.

Figure 10:
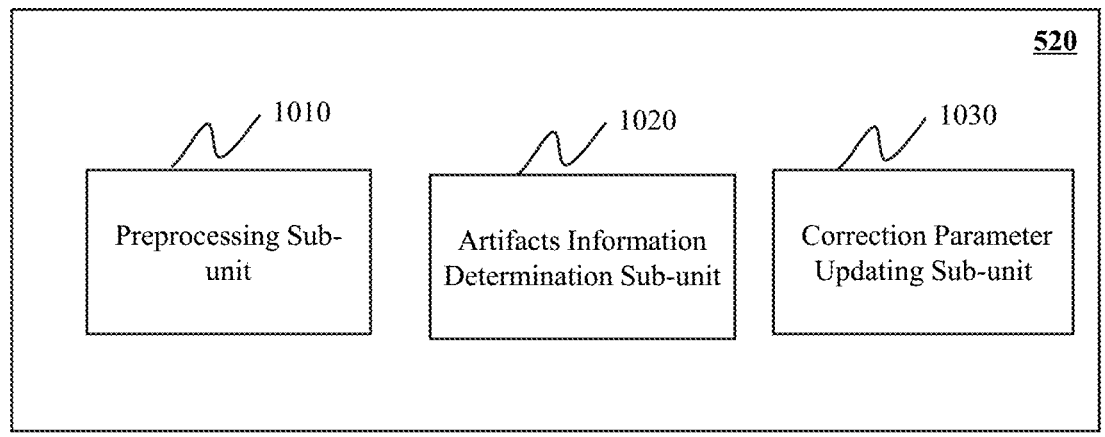
FIG. 10 is a block diagram of an exemplary updating unit 520 according to some embodiments of the present disclosure.

FIG. 10 is a block diagram of an exemplary updating unit 520 according to some embodiments of the present disclosure. As shown in FIG. 10, the updating unit 520 may include a preprocessing sub-unit 1010, an artifacts information determination sub-unit 1020, and a correction parameters updating sub-unit 1030.

The preprocessing sub-unit 1010 may preprocess the original data. The original data may include the original scanned data and/or the original images. In some embodiments, the preprocessing may include performing artifacts correction of the original data based on the original correction parameters. In some embodiments, the preprocessing unit 1010 may further generate a preprocessing result (e.g., also referred to as "the first correction data"). The preprocessing results may include the scanned data (e.g., also referred to as "pre-corrected scanned data") which has been corrected, or artifact corrected images (e.g., also referred to as a "post-corrected images").

The artifacts information determination unit 1020 may extract artifacts information. The artifacts information may refer to artifacts data contained in the original data. The artifacts information may be obtained from the preprocessing results. For example, the artifacts information determination unit 1020 may obtain the artifacts information by comparing the original data with the preprocessing results. As another example, the artifacts information may refer to artifacts data that is eliminated or weakened from the original data. In some embodiments, the artifacts information may include an artifacts intensity.

The correction parameters updating sub-unit 1030 may update the correction parameters according to the artifacts information. In some embodiments, the correction parameters may include an air correction table or a marked damaged channel. In some embodiments, the correction parameters updating sub-unit 1030 may send instructions to the operational control computer device 140 through the output module 460, and the operation computer device 140 may control the display device 160 or the external device (e.g., a terminal, etc.) associated with the imaging systems 100 to prompt the users (e.g., doctors, imaging technicians). The instructions may be the prompt which is sent to users of whether to update the correction parameters or the prompt which is sent to users of the types (e.g., an air correction table, a marked damaged channel, etc.) of correction parameters to be updated.

In some embodiments, the preprocessing sub-unit 1010 may be integrated in the artifacts correction unit 530. In some embodiments, the preprocessing sub-unit 1010 may be optional, and the preprocessing of the original data may be performed by the artifacts correction unit 530.

Figure 11:
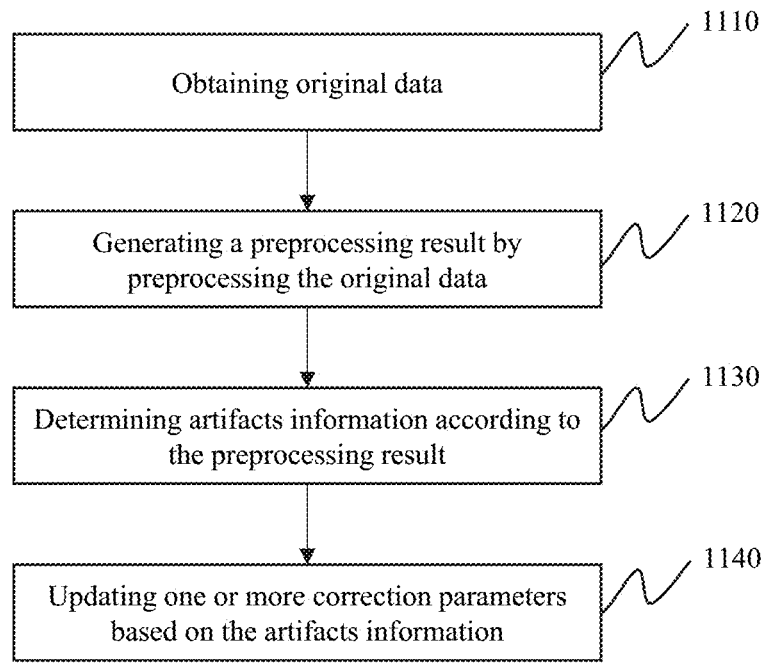
FIG. 11 is a flow chart of an exemplary process for updating correction parameters according to some embodiments of the present disclosure.

FIG. 11 is a flow chart of an exemplary process for updating correction parameters according to some embodiments of the present disclosure. In step 1110, the original data may be obtained. The process of obtaining the original data may be achieved by the original data acquisition unit 510. In step 1120, the original data may be preprocessed to get a preprocessing result. The preprocessing result may include scanned data after the artifacts correction or an image after the artifacts correction. The process of preprocessing may be performed by the preprocessing sub-unit 1010. In some embodiments, the preprocessing may include performing the artifacts correction of the original data based on the original correction parameters. In some embodiments, a pre-correction and/or a post-correction of the original data may be performed in the preprocessing process. The pre-correction described herein refers to the correction of scanned data before the image reconstruction, and the post-correction refers to the correction of images after the image reconstruction.

In step 1130, the artifacts information may be obtained based on the preprocessing results. The process of obtaining the artifacts information may be performed by artifacts information determination sub-unit 1020. The artifacts information may refer to the artifacts data contained in the original data. In some embodiments, artifacts information may be obtained from the preprocessing results. For example, the artifacts information determination sub-unit 1020 may obtain the artifacts information through comparing the original data with the preprocessing results. As another example, the artifacts information may refer to artifacts data which may be eliminated or weakened from the original data. As still another example, the artifacts information may refer to the artifacts data which is eliminated or weakened from the pre-correction of the original data, or the artifacts data which is eliminated or weakened from the post-correction of the original images. In some embodiments, the artifacts information may include an artifacts intensity.

In step 1140, the correction parameters may be updated based on the artifacts information. The process of updating the correction parameters may be performed by the correction parameters updating unit 1030. In some embodiments, the types of the correction parameters (e.g., air correction tables, labeled bad channels, etc.) that need to be updated may be determined based on the artifacts information. For example, whether to update the correction parameters and/or the types of correction parameters which need to be updated may be determined according to the artifacts intensity.

In some embodiments, the method of updating the correction parameters described in FIG. 11 may further include a step of prompting the user. Specifically, when the correction parameters need to be updated, the correction parameters updating sub-unit 1030 may send instructions to the operational control computer device 140 through the output module 460, the operational control computer device 140 may control the display device 160 and the external device (e.g., a terminal, etc.) associated with the imaging system 100 to prompt the user whether to update the correction parameters, or the types of the correction parameters (e.g., air correction tables, marked damaged channels, etc.) that need to be updated. The way of prompting may include one or more of the display of dialog box, the prompt tone, the voice prompt, etc.

Figure 12:
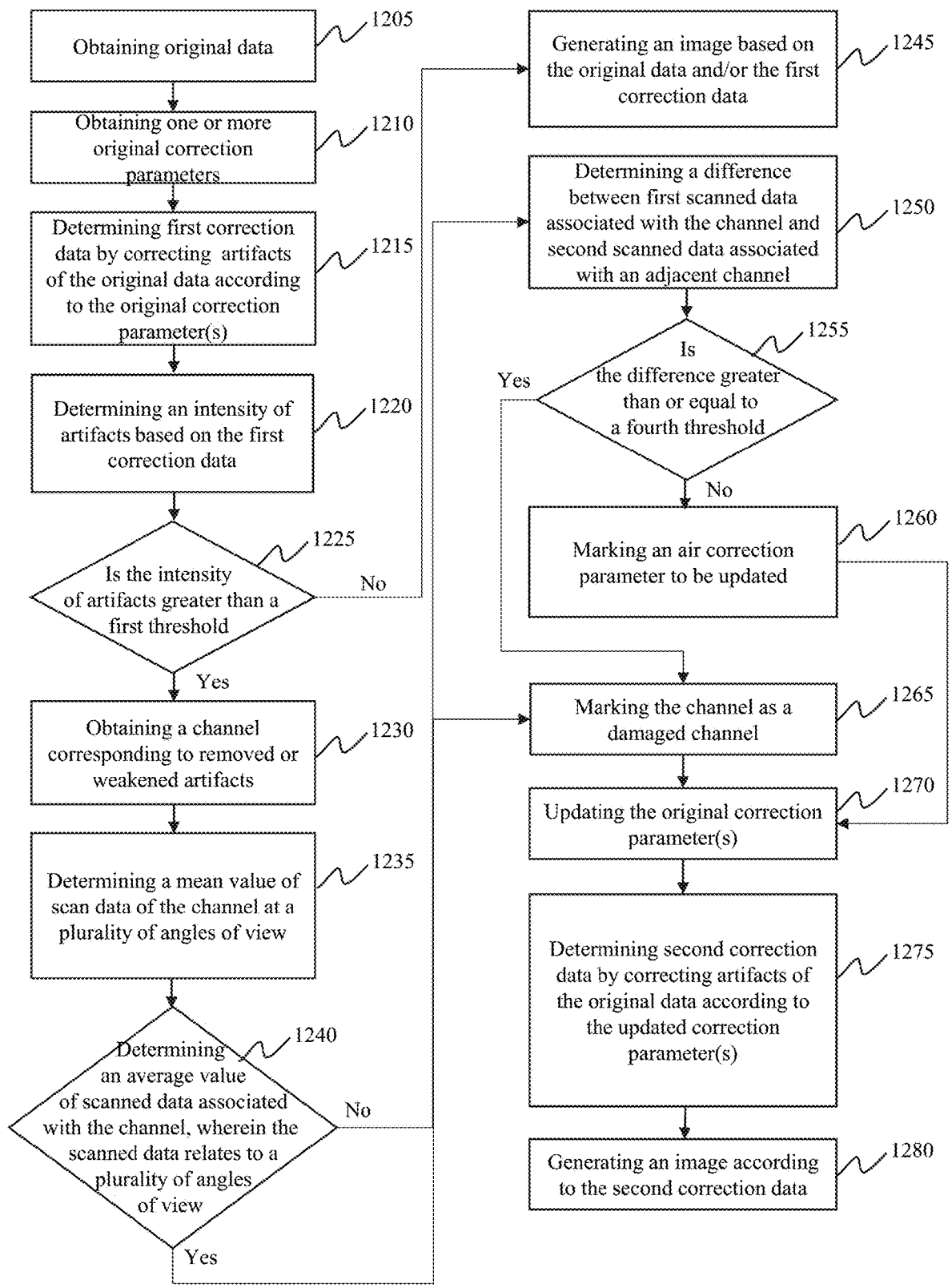
FIG. 12 is a flow chart of an exemplary process for correcting artifacts according to some embodiments of the present disclosure.

FIG. 12 is a flow chart of an exemplary process for correcting artifacts according to some embodiments of the present disclosure. In step 1205, the original data may be obtained. The process of obtaining original data may be performed by the original data obtaining unit 510. In step 1210, the original correction parameters may be obtained. The original correction parameters described herein may refer to a first air correction table corresponding to a first temperature. The process of obtaining the original correction parameters may be performed by the preprocessing sub-unit 1010. The process of obtaining the original correction parameters may be performed by the artifacts correction unit 530 when the update unit 520 omits the preprocessing sub-unit 1010 or the preprocessing sub-unit 1010 is integrated in the artifacts correction unit 530.

In step 1215, the first correction data may be obtained by correcting the original data based on the original correction parameters. The process of obtaining the first correction data may be performed by the preprocessing sub-unit 1010. The process of obtaining the first correction data may be performed by the artifacts correction unit 530 when the updating unit 520 omits the preprocessing sub-unit 1010 or when the preprocessing sub-unit 1010 is integrated in the artifacts correction unit 530. In some embodiments, the artifacts correction of the original data based on the original correction parameters may include a pre-correction and/or a post-correction. In some embodiments, the first correction data may include the data obtained by the artifacts correction of the original data based on the original correction parameters (e.g., the pre-corrected data or the post-corrected images obtained by the artifacts correction based on the original correction parameters).

In step 1220, the artifacts intensity may be obtained based on the first correction data. The process of obtaining the artifact intensity may be performed by the artifacts information determination sub-unit 1020. In some embodiments, the artifacts intensity may be the intensity of the artifacts information which is eliminated or weakened when the original correction parameters are corrected. For example, the intensity of the artifacts may refer to the intensity of the artifacts information which is eliminated or reduced when the original data is post-corrected, or the intensity of the artifacts information which is eliminated or reduced when the original data is pre-corrected and post-corrected. In some embodiments, the artifacts intensity may be obtained by comparing the original data with the first correction data. For example, the artifacts information determination sub-unit 1020 may obtain the artifacts intensity by comparing the original scanned data with the pre-corrected data. As another example, the artifacts information determination sub-unit 1020 may obtain the artifacts intensity by comparing the original images with the post-corrected images (e.g., the images obtained by the post-correction of the original images).

In step 1225, whether the artifacts intensity exceeds a first threshold value may be determined. If the artifacts intensity exceeds the first threshold, step 1230 may be executed; if the artifacts intensity does not exceed the first threshold, step 1245 may be executed. The process of determining whether the artifacts intensity exceeds the first threshold value may be performed by the correction parameters updating sub-unit 1030. In step 1245, images may be obtained based on the original data or the first correction data. The process of obtaining the images based on the original data or the first correction data may be performed by the image reconstruction module 420. In some embodiments, the first threshold may be the upper limit of the artifacts intensity processed by the original correction parameters. The unit of the first threshold may be CT unit (Hounsfield Unit, HU). In step 1230, the channels corresponding to the artifacts information that is eliminated or weakened may be determined.

In step 1235, the average value of the scanned data of the channel at a plurality of angles of view (e.g., each angle of view) may be obtained. For example, the average value may be obtained according to Equation (3):

$$V_{0m} = \frac{\sum_{i=1}^{VN} chan_B(i)}{VN}, i \in [1, VN], \tag{3}$$

where $V_{0m}$ may represent the average value; $chan_B(i)$ may represent the scanned data of the channel at the ith angle of view; and VN may represent the number of all the angles. In some embodiments, VN may be the number of the sampling angle of view of at least half a lap or a lap.

In step 1240, whether the average value is greater than or equal to a second threshold, or less than or equal to a third threshold may be determined. If the average value is greater than or equal to a second threshold, or less than or equal to the third threshold, step 1265 may be executed and the channel may be marked as a damaged channel; if the average threshold value is less than the second threshold and greater than the third threshold, step 1250 may be executed. In some embodiments, the second threshold and the third threshold may be the preset value based on the detector performance. For example, the second threshold and the third threshold may represent the maximum and minimum values of the detector in a certain range, respectively.

In step 1250, a difference between the scanned data of the channel and the data of its adjacent channel may be obtained. For example, firstly the linear interpolation of scanned data in multiple angles of view (e.g., each angle of view of the adjacent channel) of the channel and its adjacent channel may be obtained, then the difference may be obtained according to the scanned data in multiple angles of view of the channel and the linear interpolation. Specifically, the linear interpolation may be obtained according to Equation (4):

$$V_1(i)=0.5*(chan_{BP}(i)+chan_{BM}(i)), i \in [1, VN], \quad (4)$$

where $V_1(i)$ may represent the linear interpolation; and $chan_{BP}(i)$ and $chan_{BM}(i)$ may represent the scanned data of the adjacent channel of $chan_B(i)$ in the ith angle of view.

The difference may be obtained according to Equation (5):

$$var = \sqrt[2]{\frac{\sum_{i=1}^{VN}\left(\frac{chan_B(i)-V_1(i)}{mA(i)}\right)^2}{VN}}, \quad (5)$$

where var may represent the difference; and mA(i) may represent a luminous flux value of the nominal bulb tube of the ith sampling obtained from the scanned data.

As another example, a spline interpolation may be firstly obtained according to the scanned data of at least three other channels around the channel, then the difference may be obtained according to the scanned data of the channel in multiple angles of view and the spline interpolation. Specifically, the spline interpolation may be obtained according to Equation (6):

$$V_2(i)=spline(chan_{BP-2}(i), chan_{BP-1}(i), chan_{BM+1}(i)), \quad (6)$$

where $V_2(i)$ may represent the spline interpolation; spline(x) may represent a function of spline interpolation; and $chan_{BP-2}(i)$, $chan_{BP-1}(i)$ and $chan_{BM+1}(i)$ may represent the scanned data of the adjacent channel of said channel in the ith angle of view.

The difference may be obtained according to Equation (7):

$$var = \left|\frac{\sum_{i=1}^{VN}[(chan_B(i)-V_{0m})*(V_2(i)-V_{1m})]}{\sum_{i=1}^{VN}(chan_B(i)-V_{0m})*\sum_{i=1}^{VN}(V_2(i)-V_{1m})}\right|, \quad (7)$$

where $V_{1m}$ may represent the average value of $V_1(i)$ in VN angles of view. In some embodiments, $V_{1m}$ may be obtained according to Equation (8):

$$V_{1m} = \frac{\sum_{i=1}^{VN} V_1(i)}{VN}, i \in [1, VN] \quad (8)$$

In step 1255, whether the difference is greater than or equal to a fourth threshold may be determined. If the difference is greater than or equal to the fourth threshold, step 1265 may be executed to mark the damaged channel; if the difference is less than the fourth threshold, step 1260 may be executed to mark the air correction parameters that need to be updated. In some embodiments, the fourth threshold may refer to a difference threshold between the signal intensity of a channel with artifacts and the signal intensity of its adjacent channel. In some embodiments, the fourth threshold may be the default value of the system 100. For example, the imaging system 100 may determine the channel to be a damaged channel when the difference between the signal intensity of a channel and the signal intensity of the adjacent channel is greater than the fourth threshold.

In step 1270, the correction parameters may be updated. In some embodiments, step 1225-step 1270 may be executed by the correction parameters updating sub-unit 1030. In some embodiments, correction parameters may be updated by performing an air scanning. In some embodiments, an air correction table (e.g., the first air correction table) corresponding a temperature may be updated to generate a new air correction table corresponding to the new temperature, for example, the air correction table corresponding to a temperature may be updated by implementing an air scanning. For example, an air correction table corresponding to the new temperature may be generated according to the methods described in FIG. 8 or FIG. 9. In some embodiments, the updating correction parameters may include updating the marked damaged channels.

In step 1275, the artifacts correction of the original data may be performed according to the updated correction parameters to obtain the second correction data. The process of obtaining the second correction data may be performed by the artifacts correction unit 530. The second correction data may refer to the data obtained after artifacts correction according to the updated correction parameters (e.g., the pre-corrected scanned data or the post-corrected images obtained based on the artifacts correction of the updated correction parameters). For example, the original data may be artifacts corrected based on the updated air correction table, or based on the air correction table corresponding to the new temperature, or the original data corresponding to the damaged channel may be corrected based on the marked damaged channel.

In step 1280, an image may be obtained based on the second correction data. The process of obtaining the image may be performed by image reconstruction module 420.

In some embodiments, the process of artifacts correction described in FIG. 12 may omit the step 1270, step 1275 or step 1280. After the correction parameters that need to be updated are marked, the marked correction parameters may not be updated until the next imaging process is performed. For example, the air correction parameters to be updated may be marked in step 1260, and an air scanning may be performed prior to the next scanning, and the marked air correction parameters may be updated according to the air scanning. As another example, the damaged channel may be marked in step 1265, and in the next imaging process, the original data corresponding to the marked damaged channel may be corrected.

In some embodiments, the artifacts correction process described in FIG. 12 may omit steps 1260 or step 1265. The operation of updating the correction parameters may be performed directly without marking the correction parameters when the correction parameters that need to be updated are determined.

In some embodiments, the method of artifacts correction described in FIG. 12 may further include the operation of prompting the user. Specifically, when the correction parameters need to be updated, the correction parameters updating sub-unit 1030 may send instructions to the operational control computer device 140 through the output module 460, and the operational control computer device 140 may control the display device 160 or the external device (e.g., a terminal, etc.) associated with the imaging system 100 to prompt the user whether to update the correction parameters. Alternatively, the operational control computer device 140 may control the display device 160 or the external device (e.g., a terminal, etc.) associated with the imaging system 100 to prompt the user the types of the correction parameters that need to be updated (e.g., the air correction table, the marked damaged channel, etc.). The method of prompting may include one or more of the display of dialog box, the prompt tone, the voice prompt, etc.

In some embodiments, the method described in FIG. 8 or FIG. 9 may be in combination with the method described in FIG. 11 or FIG. 12. For example, in the method described in FIG. 11 or FIG. 12, the correction parameters may include the air correction parameters or the marked damaged channels. The updating the air correction parameters may include updating the air correction table corresponding to a certain temperature, or generating an air correction table corresponding to a new temperature. The air correction table corresponding to a new temperature may be generated based on the method described in FIG. 8 or FIG. 9. As another example, whether the second temperature of the detector is greater than the first temperature may be determined according to the method described in FIG. 8 or FIG. 9, before the scanning which is based on the method described in FIG. 11 or FIG. 12. If the second temperature of the detector is greater than the first temperature, the air correction table corresponding to the second temperature may be generated based on the method described in FIG. 8 or FIG. 9, and the air correction table corresponding to the second temperature or the marked damaged channel may be determined whether it needs to be updated based on the method described in FIG. 8 or FIG. 9. As still another example, whether the real-time temperature of the detector is greater than first temperature may be determined at intervals (e.g., 5 minutes, 10 minutes, etc.) in the process of the method described in the FIG. 11 or FIG. 12. If the real-time temperature of the detector is greater than the first temperature, the air correction table corresponding to the real-time temperature of the detector may be generated according to the method described in FIG. 8 or FIG. 9.

In some embodiments, in the imaging process of the Nth object (e.g., the imaging process of different parts of the same body), it is not need to determine whether to update the correction parameters in the imaging process of each object. For example, the determination of whether it's need to update the correction parameters (e.g., implementing the method described in FIG. 12 for the M-th object) may be implemented when the M-th object is scanned. And for the other N-1 objects, the original data may be corrected based on the original correction parameters or the updated correction parameters (e.g., step 1205, step 1210, step 1215, and step 1245 may be executed for the other N-1 objects), wherein, M and N may be integers, M may be less than or equal to N, and M may be greater than 1 (for example, M may be equal to 2, which means the method described in FIG. 12 may be implemented for the second objects). In some embodiments, M may be equal to 1, which means the method described in FIG. 12 may be implemented for the first objects.

In some embodiments, the first threshold, the second threshold, the third threshold and the fourth threshold mentioned in the present disclosure may be a numerical range or a specific value. The first threshold, the second threshold, the third threshold and the fourth threshold may be determined according to the historical data, the default value of the imaging system 100, or the instructions of the user (e.g., a doctor, an imaging technician, etc.).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device" or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wire-line, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed object matter requires more features than are expressly recited in each claim. Rather, claim object matter lie in less than all features of a single foregoing disclosed embodiment.

In some embodiments, the numbers expressing quantities of ingredients, properties, and so forth, used to describe and claim certain embodiments of the application are to be understood as being modified in some instances by the term "about", "approximate" or "substantially". For example, "about", "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for computed tomography (CT) imaging, comprising:
   obtaining a first air correction table corresponding to a first temperature of a detector, wherein the first air correction table comprises a plurality of first air correction parameters of a plurality of sets of scan protocols at the first temperature;
   obtaining a second temperature of the detector;
   obtaining one or more second air correction parameters of one or more sets of scan protocols among the plurality of sets of scan protocols at the second temperature;
   determining an average correction parameter based on differences between the one or more second air correction parameters at the second temperature and one or more first air correction parameters of the one or more sets of scan protocols at the first temperature; and
   determining a second air correction table corresponding to the second temperature based on the second temperature, the average correction parameter, and the first air correction table, wherein the second air correction table comprises a plurality of second air correction parameters of the plurality of sets of scan protocols at the second temperature.

2. The method of claim 1, wherein the one or more sets of scan protocols include two sets of scan protocols among the plurality of sets of scan protocols.

3. The method of claim 1, wherein the obtaining the one or more second air correction parameters of the one or more sets of scan protocols among the plurality of sets of scan protocols at the second temperature includes:
   performing air scanning at the second temperature based on each of the one or more sets of scan protocols; and
   determining the one or more second air correction parameters at the second temperature according to the air scanning.

4. The method of claim 1, wherein the determining the second air correction table corresponding to the second temperature based on the second temperature, the average correction parameter, and the first air correction table includes:
   determining a sum of the average correction parameter and a first air correction parameter for each of remaining sets of the plurality of scan protocols other than the one or more sets of scan protocols at the first temperature; and
   determining a second air correction parameter for each of the remaining sets of scan protocols at the second temperature based on a sum corresponding to the each scan protocol; and
   determining the second air correction table based on the one or more second air correction parameters for the one or more sets of scan protocols and the second air correction parameters for the remaining sets of scan protocols.

5. The method of claim 1, wherein a first air correction parameter of the first correction table is configured to perform artifact correction to original data of an object acquired at the first temperature, the original data comprising scanned data or an image generated based on the scanned data.

6. The method of claim 5, wherein the original data includes CT scanned data or a CT image generated based on the CT scanned data.

7. The method of claim 5, wherein the artifact correction is configured to correct artifacts caused by at least one of improper data sampling, partial volume effect, a motion of the object, a metal object, beam hardening, noise, a spiral scan, a mechanical failure, scattering rays, extrafocal radiation, incomplete projection data, different gains in pixel units of the detector, a change of a gain of a pixel unit of the detector, or a channel fault of the detector existing in acquiring the original data.

8. The method of claim 7, wherein the artifacts include at least one of a strip artifact, a shadow artifact, an arc artifact, or a ring artifact.

9. The method of claim 1, wherein a second air correction parameter of the second correction table is configured to perform artifact correction to original data of an object acquired at the second temperature, the original data comprising scanned data or an image generated based on the scanned data.

10. The method of claim 1, wherein the first temperature is a temperature range or a specific temperature value.

11. The method of claim 1, wherein the first temperature is a normal operating temperature of the detector.

12. The method of claim 1, wherein the second temperature is a temperature range or a specific temperature value.

13. The method of claim 1, wherein the second temperature is a real-time temperature of the detector.

14. The method of claim 13, wherein the real-time temperature of the detector is an average temperature of the detector within a time period.

15. A system comprising:
   a non-transitory storage medium storing a set of instructions;
   a processor in communication with the non-transitory storage medium, wherein when executing the set of instructions, the processor is directed to perform operations including:
      obtaining a first air correction table corresponding to a first temperature of a detector, wherein the first air correction table comprises a plurality of first air correction parameters of a plurality of sets of scan protocols at the first temperature;
      obtaining a second temperature of the detector;
      obtaining one or more second air correction parameters of one or more sets of scan protocols among the plurality of sets of scan protocols at the second temperature;
      determining an average correction parameter based on differences between the one or more second air correction parameters at the second temperature and one or more first air correction parameters of the one or more sets of scan protocols at the first temperature; and
      determining a second air correction table corresponding to the second temperature based on the second temperature, the average correction parameter, and the first air correction table, wherein the second air correction table comprises a plurality of second air correction parameters of the plurality of sets of scan protocols at the second temperature.

16. The system of claim 15, wherein the one or more sets of scan protocols include two sets of scan protocols among the plurality of sets of scan protocols.

17. The system of claim 15, wherein the obtaining the one or more second air correction parameters of the one or more sets of scan protocols among the plurality of sets of scan protocols at the second temperature, the processor is directed to perform operations including:
   performing air scanning at the second temperature based on each of the one or more sets of scan protocols; and
   determining the one or more second air correction parameters at the second temperature according to the air scanning.

18. The system of claim 15, wherein the determining the second air correction table corresponding to the second temperature based on the second temperature, the average correction parameter, and the first air correction table, the processor is directed to perform operations including:
   determining a sum of the average correction parameter and a first air correction parameter for each of remaining sets of the plurality of scan protocols other than the one or more sets of scan protocols at the first temperature; and
   determining a second air correction parameters for each of the remaining sets of scan protocols at the second temperature based on a sum corresponding to the each scan protocol; and
   determining the second air correction table based on the one or more second air correction parameters for the one or more sets of scan protocols and the second air correction parameters for the remaining sets of scan protocols.

19. The system of claim 15, wherein a first air correction parameter of the first correction table is configured to perform artifact correction to original data of an object acquired at the first temperature, the original data comprising scanned data or an image generated based on the scanned data.

20. A non-transitory computer-readable medium storing at least one set of instructions, wherein when executed by at least one processor, the at least one set of instructions directs the at least one processor to perform acts of:
- obtaining a first air correction table corresponding to a first temperature of a detector, wherein the first air correction table comprises a plurality of first air correction parameters of a plurality of sets of scan protocols at the first temperature;
- obtaining a second temperature of the detector;
- obtaining one or more second air correction parameters of one or more sets of scan protocols among the plurality of sets of scan protocols at the second temperature;
- determining an average correction parameter based on differences between the one or more second air correction parameters at the second temperature and one or more first air correction parameters of the one or more sets of scan protocols at the first temperature; and
- determining a second air correction table corresponding to the second temperature based on the second temperature, the average correction parameter, and the first air correction table, wherein the second air correction table comprises a plurality of second air correction parameters of the plurality of sets of scan protocols at the second temperature.

* * * * *